US 6,658,277 B2

(12) United States Patent
Wasserman

(10) Patent No.: US 6,658,277 B2
(45) Date of Patent: Dec. 2, 2003

(54) SIGNAL PROCESSING METHOD AND DEVICE FOR SIGNAL-TO-NOISE IMPROVEMENT

(75) Inventor: Yoram Wasserman, Haifa (IL)

(73) Assignee: Imagyn Medical Technologies, Inc., Irvine, CA (US)

( * ) Notice: Subject to any disclaimer, the term of this patent is extended or adjusted under 35 U.S.C. 154(b) by 0 days.

(21) Appl. No.: 09/981,564

(22) Filed: Oct. 17, 2001

(65) Prior Publication Data

US 2003/0055324 A1 Mar. 20, 2003

(30) Foreign Application Priority Data

Sep. 13, 2001 (IL) .................................................. 145445

(51) Int. Cl.[7] .................................................. A61B 5/00
(52) U.S. Cl. ...................................... 600/323; 600/330
(58) Field of Search ................................ 600/300, 301, 600/322, 323, 330

(56) References Cited

U.S. PATENT DOCUMENTS

| 3,638,640 A | 2/1972 | Shaw |
| 3,799,672 A | 3/1974 | Vurek |
| 3,847,483 A | 11/1974 | Shaw |

(List continued on next page.)

FOREIGN PATENT DOCUMENTS

| WO | WO 9403102 | 2/1994 |
| WO | WO 0013172 | 3/2000 |
| WO | WO 0154573 | 8/2001 |
| WO | WO 0184107 | 11/2001 |

OTHER PUBLICATIONS

"Reflectance Pulse Oximetry at the Forehead of Newborns: The Influence of Varying Pressure on the Probe"; A. Carin M. Dassel, MD, et al.; Dept. of Obstetrics and Gynecology, Univ. Hospital Groningen, Groningen; Journal of Clinical Monitoring 12: pp. 421–428, 1996.

"Reflectance Pulse Oximetry—Priniciples and Obstetric Application in the Zurich System"; Voker Konig, Renate Huch, and Albert Huch; Perinatal Physiology Research Dept., Dept. of Obstetrics, Zurich Univ. Hospital, CH–8091 Zurich, Switzerland; Journal of Clinical Monitoring and Computing 14: pp. 403–412, 1998.

"Effect of location of the sensor on reflectance pulse oximetry"; A.C. M. Dassel, Research Fellow et al.; British Journal of Obstetrics and Gynecology; Aug. 1997, vol. 104, pp. 910–916.

"Design and Evaluation of a New Reflectance Pulse Oximeter Sensor"; Y. Wasserman et al., PhD, et al.; Worcester Polytechnic Institute, Biomedical Engineering Program, Worcester, MA 01609; Association for the Advancement of Medical Instrumentation, vol. 22, No. 4, 1988; pp. 167–173.

(List continued on next page.)

Primary Examiner—Eric F. Winakur
Assistant Examiner—David J. McCrosky
(74) Attorney, Agent, or Firm—Howard & Howard

(57) ABSTRACT

A method and apparatus extract a signal component of a measured signal using one of two methods. If the signal component in the measured signal is a periodic signal with a certain well-defined peak-to-peak intensity value, upper and lower envelopes of the measured signal are determined and analyzed to extract said signal component of the measured signal. This signal component can further be used to calculate a desired parameter of the sample. The DC component of the signal is determined as the median value of the upper envelope, and the AC component is determined as the median value of the difference between the upper and lower envelopes. If the signal component of the measured signal is a periodic signal characterized by a specific asymmetric shape, a specific adaptive filtering is applied to the measured signal, resulting in the enhancement of the signal component relative to a noise component. This adaptive filtering is based on a derivative of the Gaussian Kernel having specific parameters matching the characteristics of the signal component.

29 Claims, 15 Drawing Sheets

U.S. PATENT DOCUMENTS

| | | |
|---|---|---|
| 3,998,550 A | 12/1976 | Konishi et al. |
| 4,086,915 A | 5/1978 | Kofsky et al. |
| 4,167,331 A | 9/1979 | Nielsen |
| 4,266,554 A | 5/1981 | Hamaguri |
| 4,357,105 A | 11/1982 | Loretz |
| 4,407,290 A | 10/1983 | Wilber |
| 4,446,871 A | 5/1984 | Imura |
| 4,714,341 A | 12/1987 | Hamaguri et al. |
| 4,740,080 A | 4/1988 | Donohue et al. |
| 4,773,422 A | 9/1988 | Isaacson et al. |
| 4,796,636 A | 1/1989 | Branstetter et al. |
| 4,802,486 A | 2/1989 | Goodman et al. |
| 4,819,649 A | 4/1989 | Rogers et al. |
| 4,819,752 A | 4/1989 | Zelin |
| 4,854,699 A | 8/1989 | Edgar, Jr. |
| 4,859,057 A | 8/1989 | Taylor et al. |
| 4,867,557 A | 9/1989 | Takatani et al. |
| 4,892,101 A | 1/1990 | Cheung et al. |
| 4,928,692 A | 5/1990 | Goodman et al. |
| 4,934,372 A | 6/1990 | Corenman et al. |
| 4,960,126 A | 10/1990 | Conlon |
| 5,190,038 A | 3/1993 | Polson et al. |
| 5,216,598 A * | 6/1993 | Branstetter et al. ......... 600/330 |
| 5,224,478 A | 7/1993 | Sakai et al. |
| 5,348,004 A | 9/1994 | Hollub |
| 5,349,519 A | 9/1994 | Kaestle |
| 5,355,880 A | 10/1994 | Thomas et al. |
| 5,398,680 A | 3/1995 | Polson et al. |
| 5,413,100 A | 5/1995 | Barthelemy et al. |
| 5,421,329 A | 6/1995 | Casciani et al. |
| 5,482,036 A | 1/1996 | Diab et al. |
| 5,490,505 A | 2/1996 | Diab et al. |
| 5,490,506 A | 2/1996 | Takatani et al. |
| 5,517,988 A | 5/1996 | Gerhard |
| 5,533,507 A | 7/1996 | Potratz |
| 5,632,272 A | 5/1997 | Diab et al. |
| 5,645,060 A | 7/1997 | Yorkey |
| 5,685,299 A | 11/1997 | Diab et al. |
| 5,758,644 A | 6/1998 | Diab et al. |
| 5,769,785 A | 6/1998 | Diab et al. |
| 5,782,237 A | 7/1998 | Casciani et al. |
| 5,797,840 A * | 8/1998 | Akselrod et al. ........... 600/301 |
| 5,823,950 A | 10/1998 | Diab et al. |
| 5,825,672 A | 10/1998 | Brudnoy |
| 5,842,981 A | 12/1998 | Larsen et al. |
| 5,853,364 A | 12/1998 | Baker, Jr. et al. |
| 5,919,134 A | 7/1999 | Diab |
| 5,924,980 A | 7/1999 | Coetzee |
| 5,995,856 A | 11/1999 | Mannheimer et al. |
| 5,995,859 A | 11/1999 | Takahashi |
| 6,011,986 A | 1/2000 | Diab et al. |
| 6,031,603 A | 2/2000 | Fine et al. |
| 6,036,642 A | 3/2000 | Diab et al. |
| 6,067,462 A | 5/2000 | Diab et al. |
| 6,081,735 A | 6/2000 | Diab et al. |
| 6,083,172 A | 7/2000 | Baker, Jr. et al. |

OTHER PUBLICATIONS

"Skin Reflectance Pulse Oximetry: In Vivo Measurements from the Forearm and Calf"; Y. Wasserman et al., PhD and M.J. McGinn, MSc; Dept. of Biomedical Engineering, Worcester Polytechnic Institute, Worcester, MA 01609; Journal of Clinical Monitoring, vol. 7, No. 1, 1991; pp. 7–12.

"Experimental and Clinical Evaluation of a Noninvasive Reflectance Pulse Oximeter Sensor"; Setsuo Takatani, PhD, et al.; Dept. of Surgery, Baylor College of Medicine, One Baylor Plaza, Houston, TX 77030; Journal of Clinical Monitoring, vol. 8, No. 4, Oct. 1992; pp. 257–266.

"Wavelength Selection for Low–Saturation Pulse Oximetry"; Paul D. Mannheimer, et al.; IEEE Transactions on Biomedical Engineering, vol. 44, No. 3, Mar. 1997; pp. 148–158.

"Noninvasive Pulse Oximetry Utilizing Skin Reflectance Photoplethysmography"; Yitzhak Wasserman et al. and Burt D. Ochs; IEEE Transactions on Biomedical Engineering, vol. 35, No. 10, Oct. 1988; pp. 798–805.

"Physio–optical considerations in the design of fetal pulse oximetry sensors"; P.D. Mannheimer, M.E. Fein and J.R. Casciani; European Journal of Obstetrics & Gynecology and Reproductive Biology 72 Suppl. 1 (1997) S9–S19.

"Fetal pulse oximetry: influence of tissue blood content and hemoglobin concentration in a new in–vitro model"; Thomas Edrich, Gerhard Rall, Reinhold Knitza; European Journal of Obstetrics & Gynecology and Reproductive Biology 72 Suppl. 1 (1997) S29–S34.

* cited by examiner

SIGNAL PROCESSING METHOD AND DEVICE FOR SIGNAL-TO-NOISE IMPROVEMENT

FIELD OF THE INVENTION

This invention is generally in the field of signal-to-noise improvement techniques, and relates to a method and device for processing a periodic signal. The present invention is particularly useful in pulse oximeters or other non-invasive measurement devices for determining oxygen saturation and/or cardiac output.

BACKGROUND OF THE INVENTION

Signal processing is an intrinsic procedure of any measurement technique, and always requires sufficient signal-to-noise ratio to enable extraction of a signal component indicative of a desired parameter from a noise component contained in the measured signal. For example, measurement techniques aimed at determining physiological parameters consist of detecting and analyzing a signal response, e.g., light response, of a sample to the application of an external field, e.g., electromagnetic radiation, and typically require suitable signal processing to extract the signal component in the detected response.

Various techniques for non-invasive measurements of blood parameters have been developed. One of such techniques is the so-called "bio-impedance technique" consisting of the following. A current source produces an alternating current, which is applied to the body through electrodes, and voltage induced by this current passage through the body is measured at additional electrodes. Other techniques utilize spectrophotometry consisting of illumination of a body part by incident light of various wavelengths and measurement of an absorption spectrum.

The most popular spectrophotometric techniques are oximetry and pulse oximetry. Oximetry is based on the strong dependence of the optical property of blood in the visible (between 500 and 700 nm) and near-infrared (between 700 and 1000 nm) spectra on the amount of oxygen in blood. Pulse oximetry, which utilizes transmission and reflection modes, relies on the detection of a photoplethysmographic signal caused by variations in the quantity of arterial blood associated with periodic contraction and relaxation of a patient's heart. The magnitude of this signal depends on the amount of blood ejected from the heart into the peripheral vascular bed with each systolic cycle, the optical absorption of the blood, absorption by skin and tissue components, and the specific wavelengths that are used to illuminate the tissue. Oxyhemoglobin saturation ($SaO_2$) is determined by computing the relative magnitudes of red (R) and infrared (IR) photoplethysmograms.

Electronic circuits, or suitable software (algorithm) inside the pulse oximeter, separate the R and IR photoplethysmograms into their respective pulsatile (AC) and non-pulsatile (DC) signal components. An algorithm inside the pulse oximeter performs a mathematical normalization by which the time-varying AC signal at each wavelength is divided by the corresponding time-invariant DC component which results mainly from the light absorbed and scattered by the bloodless tissue, residual arterial blood when the heart is in diastole, venous blood and skin pigmentation. Since it is assumed that the AC portion results only from the arterial blood component, this scaling process provides a normalized R/IR ratio, i.e., the ratio of AC/DC values corresponding to R- and IR-spectrum wavelengths, respectively, which is highly dependent on $SaO_2$, but is largely independent of the volume of arterial blood entering the tissue during systole, skin pigmentation, skin thickness and vascular structure.

Pulse oximetry operating in reflection mode, while being based on similar spectrophotometric principles as that of transmission mode, is more challenging to perform and has unique problems that cannot always be solved by solutions suitable for solving the problems associated with transmission-mode pulse oximetry. Generally, when comparing transmission and reflection pulse oximetry, the problems associated with reflection pulse oximetry consist of the following. In reflection pulse oximetry, the pulsatile AC signals are generally very small and, depending on sensor configuration and placement, have larger DC components as compared to those of transmission pulse oximetry. In addition to optical absorption and reflection due to blood, the DC signal of the R and IR photoplethysmograms in reflection pulse oximetry can be adversely affected by strong reflections from a bone. This problem becomes more apparent when applying measurements at such body locations as the forehead and the scalp, or when the sensor is mounted on the chest over the ribcage. Similarly, variations in contact pressure between the sensor and the skin can cause larger errors in reflection pulse oximetry (as compared to transmission pulse oximetry) since some of the blood near the superficial layers of the skin may be normally displaced away from the sensor housing towards deeper subcutaneous structures. Consequently, the highly reflective bloodless tissue compartment near the surface of the skin can cause significant errors even at body locations where the bone is located too far away to influence the incident light generated by the sensor.

Another problem with reflectance sensors currently available is the potential for specular reflection caused by the superficial layers of the skin, when an air gap exists between the sensor and the skin, or by the direct shunting of light between the LEDs and the photodetector through a thin layer of fluid (which may be due to excessive sweating or from amniotic fluid present during delivery).

It is important to keep in mind the two fundamental assumptions underlying conventional dual-wavelength pulse oximetry: The path of light rays with different illuminating wavelengths in tissue are substantially equal, and therefore, cancel each other. Each light source illuminates the same pulsatile change in arterial blood volume. Furthermore, the correlation between optical measurements and tissue absorption in pulse oximetry are based on the fundamental assumption that light propagation is determined primarily by absorbance due to Lambert-Beer's law neglecting multiple scattering effects in biological tissues. In practice, however, the optical paths of different wavelengths in biological tissues are known to vary more in reflectance oximetry compared to transmission oximetry, since they strongly depend on the light scattering properties of the illuminated tissue and sensor mounting.

The relevant in vivo studies are disclosed, for example, in the following publications:

Dassel, et al., "Effect of location of the sensor on reflectance pulse oximetry", British Journal of Obstetrics and Gynecology, vol. 104, pp. 910–916, (1997);

Dassel, et al., "Reflectance pulse oximetry at the forehead of newborns: The influence of varying pressure on the probe", Journal of Clinical Monitoring, vol. 12, pp. 421–428, (1996).

It should be understood that the signal-to-noise ratio improvement is also needed in tissue simulated model measurements (in vitro). The problems arising with in vitro measurements are disclosed, for example in the following publication: Edrich et al., "Fetal pulse oximetry: influence of tissue blood content and hemoglobin concentration in a new in-vitro model", European Journal of Obstetrics and Gynecology and Reproductive Biology, vol. 72, suppl. 1, pp. S29–S34, (1997).

Improved sensors for application in dual-wavelength reflectance pulse oximetry have been developed, and are disclosed, for example, in the following publication: Mendelson, et al., "Noninvasive pulse oximetry utilizing skin reflectance photoplethysmography", IEEE Transactions on Biomedical Engineering, vol. 35, no. 10, pp. 798–805 (1988). According to this technique, the total amount of backscattered light that can be detected by a reflectance sensor is directly proportional to the number of photodetectors placed around the LEDs. Additional improvements in signal-to-noise ratio were achieved by increasing the active area of the photodetector and optimizing the separation distance between the light sources and photodetectors.

A different approach, based on the use of a sensor having six photodiodes arranged symmetrically around the LEDs, is disclosed in the following publications:

Mendelson, et al., "Design and evaluation of a new reflectance pulse oximeter sensor", Medical Instrumentation, vol. 22, no. 4, pp. 167–173 (1988); and Mendelson, et al., "Skin reflectance pulse oximetry: in vivo measurements from the forearm and calf", Journal of Clinical Monitoring, vol. 7, pp. 7–12, (1991).

According to this approach, in order to maximize the fraction of backscattered light collected by the sensor, the currents from all six photodiodes are summed electronically by internal circuitry in the pulse oximeter. This configuration essentially creates a large area photodetector made of six discrete photodiodes connected in parallel to produce a single current that is proportional to the amount of light backscattered from the skin.

A reflectance sensor based on the use of eight dual-wavelength LEDs and a single photodiode is disclosed in the following publication: Takatani et al., "Experimental and clinical evaluation of a noninvasive reflectance pulse oximeter sensor", Journal of Clinical Monitoring, vol. 8, pp. 257–266 (1992). Here, four R and four IR LEDs are spaced at 90-degree intervals around the substrate and at an equal radial distance from the photodiode. A similar sensor configuration based on six photodetectors mounted in the center of the sensor around the LEDs is disclosed in the following publication: Konig, et al., "Reflectance pulse oximetry—principles and obstetric application in the Zurich system", Journal of Clinical Monitoring, vol. 14, pp. 403–412 (1998).

Pulse oximeter probes of the type comprising three or more LEDs for filtering noise and monitoring other functions, such as carboxyhemoglobin or various indicator dyes injected into the blood stream, have been developed and are disclosed, for example, in WO 00/32099 and U.S. Pat. No. 5,842,981. The techniques disclosed in these publications are aimed at providing an improved method for direct digital signal formation from input signals produced by the sensor and for filtering noise.

As indicated above, in pulse oximetry, $SpO_2$ and the heart rate are calculated from the detected signal, which is relatively small with a reflection-mode pulse oximeter. Methods for processing the signals detected by a pulse oximeter are described in the following U.S. Pat. Nos. 5,482,036; 5,490,505; 5,685,299; 5,632,272; 5,769,785; 6,036,642; 6,081,735; 6,067,462; and 6,083,172. These methods, however, utilize a specific model based on certain assumptions of noise reference.

SUMMARY

There is a need in the art to improve the signal-to-noise ratio (SNR) in measured data by providing a novel method for processing a measured signal, which has certain known characteristics.

The present invention is associated with the fact that the characteristics of most physiological signals are known, being for example periodic with certain well-defined peak-to-peak intensity value (such as a pulsatile blood-related signal), or periodic with a specific asymmetric shape (such as blood pressure pulse or ECG). On the contrary, a noise component in the measured signal is typically associated with artifacts of various kinds, and therefore has no specific characteristics.

The main idea of the present invention is as follows. The time variation of a response (measured signal or measured data) of a sample to the application of an external field is detected by any suitable means and a measured signal representative of the response is generated. If a signal component in the measured signal is a periodic signal with a certain well-defined peak-to-peak intensity value, upper and lower envelopes of the measured signal are determined and analyzed to extract said signal component of the measured signal. This signal component can further be used to calculate a desired parameter of the sample. The DC component of the signal is determined as the median value of the upper envelope, and the AC component is determined as the median value of the difference between the upper and lower envelopes. If a signal component of the measured signal is a periodic signal characterized by a specific asymmetric shape, a specific adaptive filtering is applied to the measured signal, resulting in the enhancement of the signal component relative to a noise component. This adaptive filtering is based on a derivative of the Gaussian Kernel having specific parameters matching the characteristics of the signal component.

The term "measured signal" used herein signifies a signal obtained by any measurement device and including a signal component, which is to be extracted and further used for determining a desired parameter, and a noise component caused by various noise and artifact conditions. The term "measured data" used herein refers to data indicative of two measured signals of different kinds. One kind of a measured signal suitable to be processed by the technique of the present invention is such containing a signal component in the form of a periodic signal with well-defined peak-to-peak value, e.g., sinusoidal-like signal. The other kind of a measured signal suitable to be processed by the technique of the present invention is one containing a signal component in the form of a periodic signal characterized by a specific asymmetric shape. Such a periodic asymmetrically shaped signal is characterized by the following: each cycle (period) of the signal contains a region including frequencies higher than those of the other regions. The present invention consists of a signal processing technique that can be carried out by a corresponding data processing and analyzing utility incorporated in a control unit of the measurement device, or in a separate unit connectable to the measurement device to receive and process the output thereof There is thus provided, according to one broad aspect of the present invention, a method for processing a measured signal to extract a signal component and suppress a noise component of the measured signal, wherein the signal component is a substantially periodic signal characterized by a substantially well-defined peak-to-peak intensity value, the method comprising the steps of:

(i) determining upper and lower envelopes of the measured signal; and (ii) analyzing the upper and lower envelope values to extract said signal component from the measured signal.

The analysis of the upper and lower envelope values comprises determining of a median of the difference between the upper and lower envelope values, as an alternating value in the signal component, and a median of the upper envelope (or a median of the upper envelope plus the lower envelope divided by two) as a constant value in the signal component. The measured signal may be a physiological signal, such as a pulsatile blood-related signal, in which case the extracted signal component is further used to determine a desired physiological parameter, such as oxyhemoglobin saturation.

The measured signal can be determined as a response of a sample to an external field, for example, a light response of the sample to incident radiation.

According to another aspect of the present invention, there is provided a signal processing method for use in determining a desired parameter of a sample, the method comprising the steps of:

providing a measured signal representative of a response of said sample to an external field, the measured signal comprising a signal component indicative of said desired parameter, and a noise component, said signal component being a substantially periodic signal characterized by a substantially well-defined peak-to-peak intensity value;

determining upper and lower envelopes of the measured signal; and analyzing the upper and lower envelope values to extract said signal component from the measured signal.

The providing of said measured signal may comprise sampling and frequency filtering of said response.

According to yet another aspect of the present invention, there is provided a method for processing a measured signal to enhance a signal component relative to a noise component in the measured signal, wherein the signal component is characterized by a specific asymmetric shape, the method comprising the steps of:

defining a kernel function being a derivative of a Gaussian with parameters matching the characteristics of said signal component; and applying filtering to the measured signal with said kernel function parameters, thereby enhancing the signal component relative to the noise component in the filtered measured signal.

According to yet another aspect of the present invention, there is provided a computer program storage device readable by a machine, tangibly embodying a program of instructions executable by a machine to perform method steps of processing a measured signal to extract a signal component and suppress a noise component of the measured signal, wherein the signal component is a substantially periodic signal characterized by a substantially well-defined peak-to-peak intensity value, which method comprises the steps of:

(i) determining upper and lower envelopes of the measured signal; and (ii) analyzing the upper and lower envelope values to extract said signal component from the measured signal.

According to yet another aspect of the present invention, there is provided a computer program storage device readable by a machine, tangibly embodying a program of instructions executable by a machine to perform method steps of processing a measured signal to enhance a signal component relative to a noise component in the measured signal, wherein the signal component is characterized by a specific asymmetric shape, which method comprises the steps of:

defining a kernel function being a derivative of a Gaussian with parameters matching the characteristics of said signal component; and applying filtering to the measured signal with said kernel function parameters, thereby enhancing the signal component relative to the noise component in the filtered measured signal.

The present invention, according to yet another aspects thereof, provides a control unit to be used with a measurement device and being preprogrammed to carry out the method of the present invention, a measurement system to be applied to a sample or medium to determine a desired parameter thereof by carrying out a method of the present invention, and a pulse oximeter utilizing such a control unit for non-invasive measurement of blood-related parameters.

More specifically, the present invention is used in non-invasive measurements of blood parameters and is therefore described below with respect to this application. It should, however, be understood that the present invention presents a method and utility for signal processing suitable for use in various applications (e.g., in vivo or in vitro measurements in a biological sample), provided that the signal component to be extracted from the measured signal for further analysis is either a substantially periodic signal with a well-defined peak-to-peak value, or a substantially periodic signal characterized by a specific asymmetric shape as defined above.

BRIEF DESCRIPTION OF THE DRAWINGS

Other advantages of the present invention will be readily appreciated as the same becomes better understood by reference to the following detailed description when considered in connection with the accompanying drawings wherein:

In order to understand the invention and to see how it may be carried out in practice, a preferred embodiment will now be described, by way of non-limiting example only, with reference to the accompanying drawings, in which:

FIGS. 2A and 2B illustrate experimental results of the method according to the invention used with the pulse oximetry, wherein FIG. 2A shows the envelope detection technique, and FIG. 2B shows how this technique can be used to extract the pulse amplitude (AC) from the detected signal;

FIGS. 5A and 5B illustrate experimental results of the method according to the invention used with the bio-impedance technique, wherein FIG. 5A shows the envelope detection technique, and FIG. 5B shows how this technique can be used to extract the pulse amplitude (AC) from the detected signal;

DETAILED DESCRIPTION OF THE INVENTION

Figure 1A:
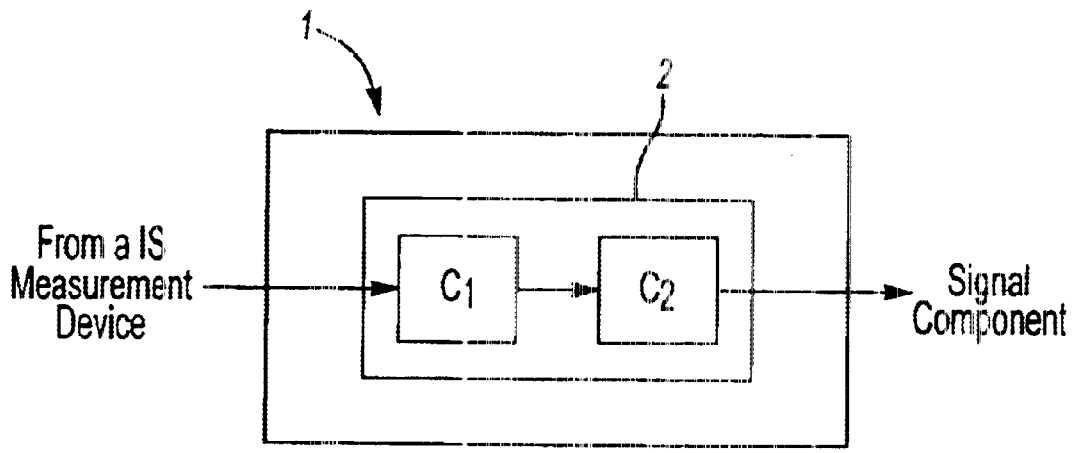
FIGS. 1A and 1B illustrate a block diagram and a flow chart of main operation steps, respectively, of a control unit according to the invention.
Figure 1B:
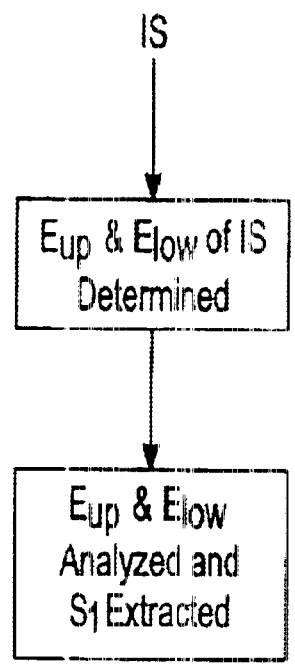

With reference to the FIGS. 1A and 1B, and in operation, the present invention provides a method and device for processing a measured signal. More specifically, the present invention extracts a signal component from the noise component and suppresses a noise component.

A control unit, generally designated 1, constructed and operated according to the invention for processing an input signal IS coming from a measurement device comprises a data processing and analyzing utility 2 having two software modules (components) $C_1$ and $C_2$ operating together to extract or enhance a signal component and suppress a noise component contained in the input signal. The software component $C_1$ processes the input signal, and the software component $C_2$ analyzes the processed data to either extract or enhance the signal component.

As shown in FIG. 1B, when a signal component $S_1$ in the form of a periodic signal with well-defined peak-to-peak value, e.g., sinusoidal-like signal, is to be extracted from the input measured signal IS, the processing of the measured signal includes determination of upper and lower envelopes $E_{up}$ and $E_{low}$ thereof (step 4), which are then analyzed to extract this signal component $S_1$ from a noise component (step 6).

If a signal component to be enhanced relative to a noise component is a periodic signal characterized by a specific asymmetric shape (i.e., each cycle (period) of the signal component contains a region including frequencies higher than those of the other regions), the data processing and analyzing utility 2 operates to define a specific kernel function (a derivative of a Gaussian with parameters matching the characteristics of the asymmetrically shaped signal component), and apply filtering to the measured signal with these kernel function parameters, thereby enhancing the signal component relative to the noise component in the filtered measured signal.

Figure 1C:
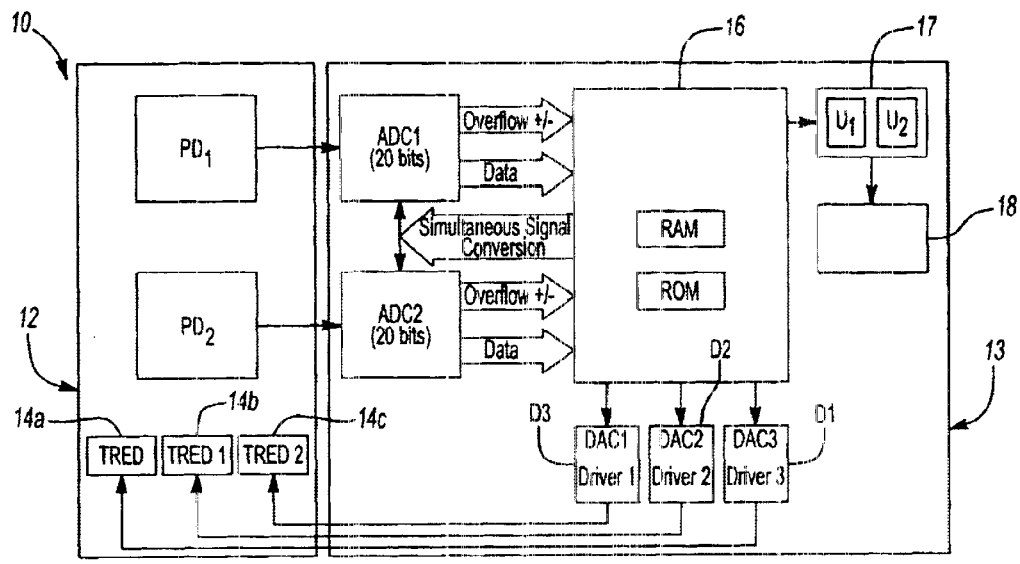
FIGS. 1C and 1D illustrate block diagrams of pulse oximetry and bio-impedance based systems, respectively, utilizing the present invention.

Referring to FIG. 1C, the present invention will now be described in the context of a measurement system 10 for non-invasive measurement of physiological parameters. It should be understood that the application of the present invention to such a measurement system 10 is for discussion purposes only and the present invention is not limited to such applications. The present invention has equal application to other uses where signal component of the kind specified is to be extracted from a measured containing a noise component.

In the present example, the system 10 is a reflectance pulse oximeter applied to a measurement location (not shown) on the patient's body and operable to detect a light response (reflection) of the measurement location and determine oxyhemoglobin saturation in the patient's blood and the heart rate. The system 10 comprises such main constructional parts as a measurement device 12 (probe) and a control unit 13.

The measurement device 12 comprises an illuminator and a detector unit. In the present example, the illuminator is composed of three light emitting elements (e.g., LEDs) 14A, 14B and 14C operated by three drivers D1–D3, respectively. LEDs 14A–14C illuminate the measurement location with three different wavelengths: one wavelength $\lambda 1$ lying in the red spectrum and the two other wavelengths $\lambda 2$ and $\lambda 3$ lying in a spectrum range including near infrared and infrared spectrum of radiation. Wavelengths $\lambda 2$ and $\lambda 3$ are selected to coincide with a spectral region of the optical absorption curve, where oxyhemoglobin ($HbO_2$) absorbs slightly more light than deoxyhemoglobin (Hb), and where the extinction coefficients of Hb and $HbO_2$ are nearly equal and remain relatively constant as a function of wavelength. The detector unit comprises two photodetectors $PD_1$ and $PD_2$, which receive light components reflected from the measurement location and generate measured data (current) indicative thereof It should be noted, although not specifically shown, that the photodetectors 14A,14B,14C are preferably designed and arranged so as to provide collection of light reflected from the measurement location at different detection points arranged along closed paths around the light emitting elements. For example, the photodetectors are two concentric rings (the so-called "near" and "far" rings), and the light emitting elements are located at the center of the rings. This arrangement enables optimal positioning of the detectors for high quality measurements, and enables distinguishing between photodetectors receiving "good" information (i.e., AC and DC values which would result in accurate calculations of $SpO_2$) and "bad" information (i.e., AC and DC values which would result in inaccurate calculations of $SpO_2$).

The operation of the measurement device and calculation of a blood parameter (e.g., oxyhemoglobin saturation) do not form part of the present invention, and therefore need not be specifically described, except to note the following. In this specific example of three wavelengths of incident radiation and a plurality of detection points, data indicative of AC/DC ratio in the light detected at each of the detection points for the three wavelengths is calculated, and analyzed to determine accepted detection points and select corresponding AC/DC ratios for each of three wavelengths. These selected ratios are then utilized to calculate the blood parameter. The analysis consists of the following: Values of the ratio $W_2/W_3$ ($W_2=I_2(AC)/I_2(DC)$ and $W_3=I_3(AC)/I_3(DC)$, I being the intensity) for the accepted detection points in at least one closed path are calculated. Each of these values is analyzed to determine whether it satisfies a certain predetermined condition (e.g., the calculated value $W_2/W_3$ is inside a predetermined range defined by a threshold value), and generate a signal indicative of whether the position of the probe (sensor) is to be adjusted or not. If the condition is satisfied, the quality of a photoplethysmogram is analyzed to determine whether it is acceptable or not. If the quality is acceptable, the selected ratios are analyzed to calculate ratios $W_1/W_2$ and $W_1/W_3$ (wherein $W_1=I_1(AC)/I_1(DC)$) from the data detected in at least one closed path, and calculate the differences $ABS(W_1/W_2-W_1/W_3)$. The calculated differences are analyzed to determine whether each of the differences satisfies a certain predetermined condition (e.g., the calculated difference $ABS(W_1/W_2-W1/W_3)$ is less than a certain threshold value for determining the blood parameter if the condition is satisfied.

As further shown in FIG. 1C, outputs of the photodetectors $PD_1$ and $PD_2$ are connected to analog-to-digital converters $ADC_1$ and $ADC_2$, respectively, which are connected to a micro-controller 16 to thereby enable simultaneous signal conversion by sampling the signal and band pass filtering. By this, noise having spectral components other then that of the signal component is suppressed. The control unit further comprises a processor 17 (composed of data processing and analyzing utilities $U_1$ and $U_2$) preprogrammed to carry out a signal processing according to the invention, and a display 18. The provision of two utilities $U_1$ and $U_2$ is aimed at determining both the $SpO_2$ and the heart rate, wherein $SpO_2$ is derived from a measured signal of the kind having a signal component $S_1$ in the form of a periodic signal with well-defined peak-to-peak value, and the heart rate is derived from a measured signal of the kind having a signal component characterized by a specific asymmetric shape.

It should be understood that for the purpose of the present invention, the light source (with respective drivers), detector, analog-to-digital converters and micro-controller constitute together a measurement device for generating data indicative of a measured signal, which includes a signal component and a noise component (noise and artifacts). Such a measurement device may be of any kind. Actually, the processor, having either one of the utilities $U_1$ and $U_2$ or both of them, may be incorporated in a separate unit connectable to the measurement device to receive and process the measured signal to thereby enable the determination of a desired parameter. For the purposes of the present invention, the signal component in the measured signal is a periodic signal with a well-defined peak-to-peak value (e.g., a pulse related signal of blood), or a signal with a specific asymmetric shape (e.g., a heart pulse signal). By using the reflectance pulse oximeter 10 applied to a location on the patient's body, the measured data contains both the signal component $S_1$ representative of the pulse related signal of the patient's blood (a substantially periodic signal with substantially well-defined peak-to-peak intensity value) and the signal component $S_2$ representative of the pulse related signal of the heart (a periodic signal characterized by a specific asymmetric shape).

Figure 1D:
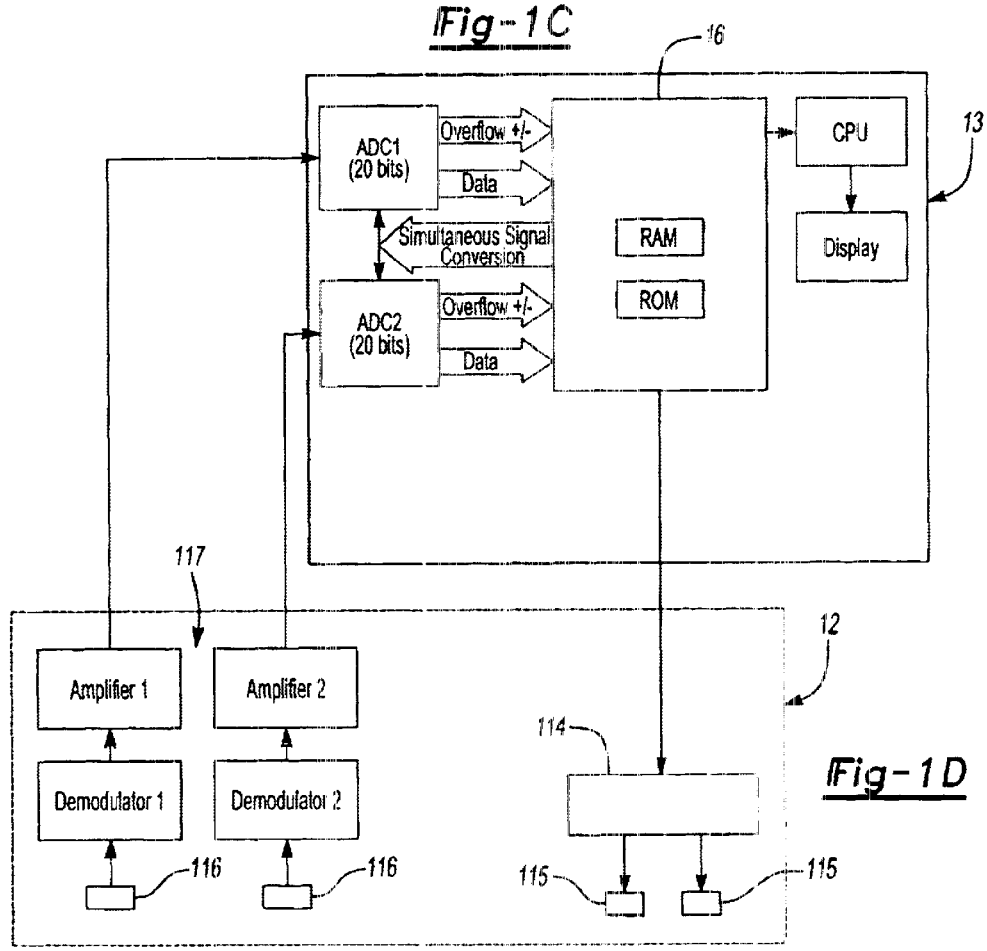

FIG. 1D illustrates a block diagram of a measurement system 100 for bio-impedance measurements. To facilitate understanding, the same reference numbers are used to identify those components that are common in the examples of FIGS. 1C and 1D. Thus, the measurement system 100 is composed of a measurement device 12 and a control unit 13, which comprises a processor 17 (composed of data processing ad analyzing utilities $U_1$ and $U_2$) preprogrammed for carrying out the method according to the invention. In the present example of FIG. 1D, the measurement device 12 comprises an alternating current source 114 operated by the micro-controller 16 to inject an electric current to the patient's body by stimulating body electrodes 115; electrodes 116 sensitive to voltage induced by the injected alternating current; and electronic components 117 (demodulators and amplifiers) for detecting and amplifying the amplitude of the alternating voltage received from the sensing electrodes 116. In the measurement device of this kind, different electrodes' arrangements are typically used for producing the bio-impedance and ECG measured signals $MS_1$ and $MS_2$.

Figure 1E:
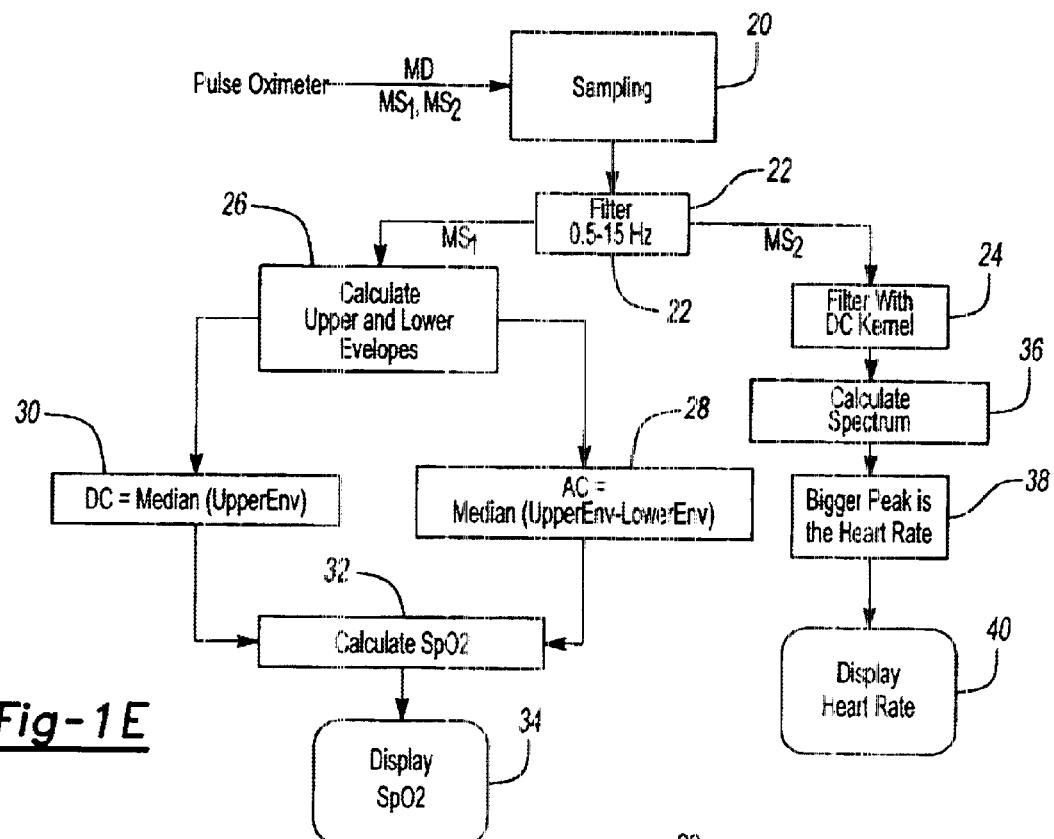
FIGS. 1E and 1F illustrate the main operational steps of a method according to the invention carried out by the systems of FIGS. 1C and 1D, respectively.
Figure 1F:
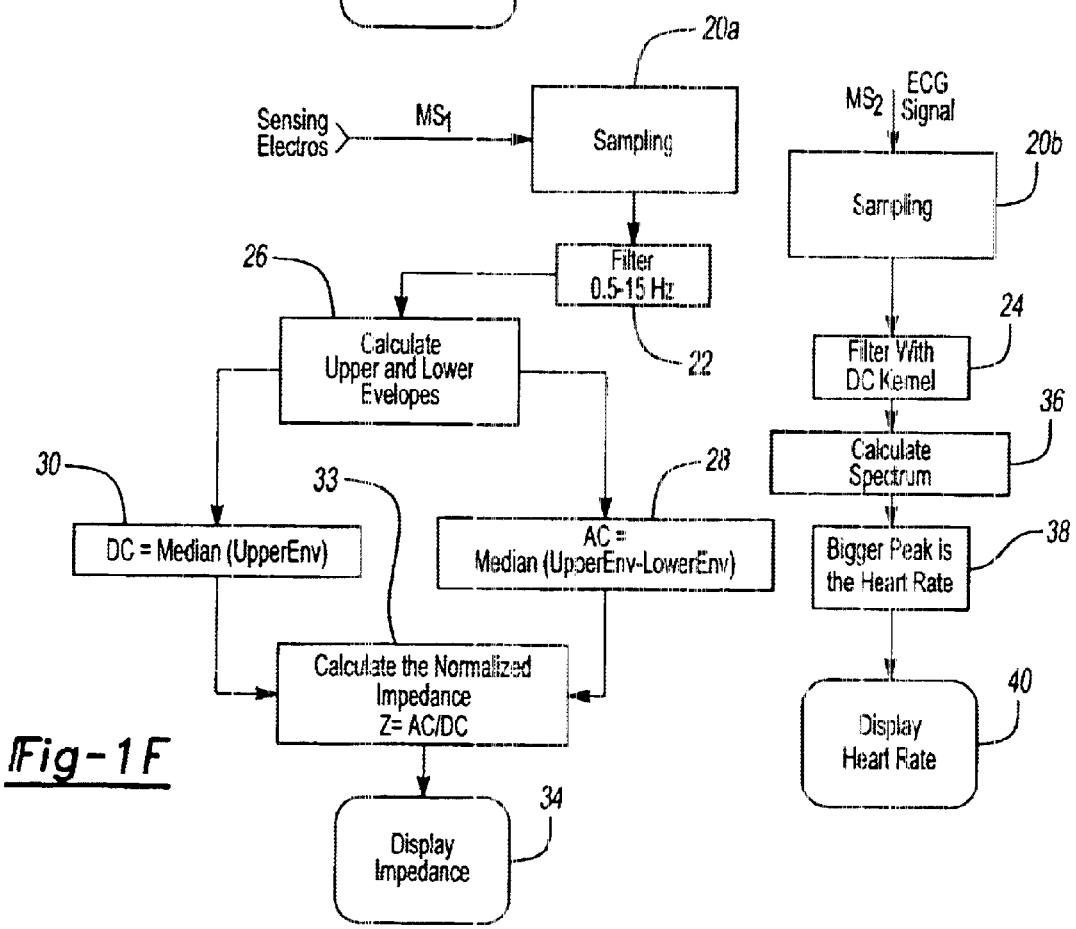

Reference is made to FIGS. 1E and 1F, illustrating the principles of the method according to the invention in the pulse oximeter and bio-impedance applications, respectively. To facilitate understanding, the same reference numbers are used to identify steps that are common in the examples of FIGS. 1E and 1F.

As shown, measured data MD received from a measurement device first undergoes sampling and frequency filtering. In the example of FIG. 1E (pulse oximetry), the measured data MD, indicative of a pulsatile blood-related signal including both the periodic signal component with well-defined peak-to-peak intensity value and the periodic signal component characterized by a specific asymmetric shape, is supplied from the measurement device of a pulse oximeter, sampled (step 20), and then undergoes frequency filtering (step 22). The measured data MD is then split so as to undergo two concurrent processes carried out by respective data processing and analyzing utilities: a processing to determine the upper and lower envelopes of the measured data MD (step 26), and filtering of the measured data MD with a specific DG Kernel, as will be described more specifically further below.

In the example of FIG. 1F, measured signals $MS_1$ and $MS_2$ (indicative of, respectively, a bio-impedance and an ECG) are supplied from different electrode arrangements of the measurement device. Consequently, the measured signals are sampled by separate sampling utilities (steps 20A and 20B). Data indicative of the sampled measured signal $MS_1$ undergoes frequency filtering (step 22), and data indicative of the sampled measured signal $MS_2$ undergoes DG kernel filtering (step 24). The frequency-filtered measured signals $MS_1$ is processed to calculate upper and lower envelopes thereof (step 26).

The upper and lower envelopes are used to determine AC and DC components of a pulsatile blood-related signal component of the measured signal (steps 28 and 30). The so-determined AC and DC components are used to calculate oxyhemoglobin saturation $SpO_2$ (step 32 in FIG. 1E), or the normalized impedance $Z=AC/DC$ (step 33 in FIG. 1F), and the calculation results are then displayed (step 34). The DG Kernel filtered data is processed to calculate the spectrum (step 36), which is analyzed to determine the biggest peak which is the heart rate (step 38). The calculation results are presented on the display (step 40).

Figure 2A:
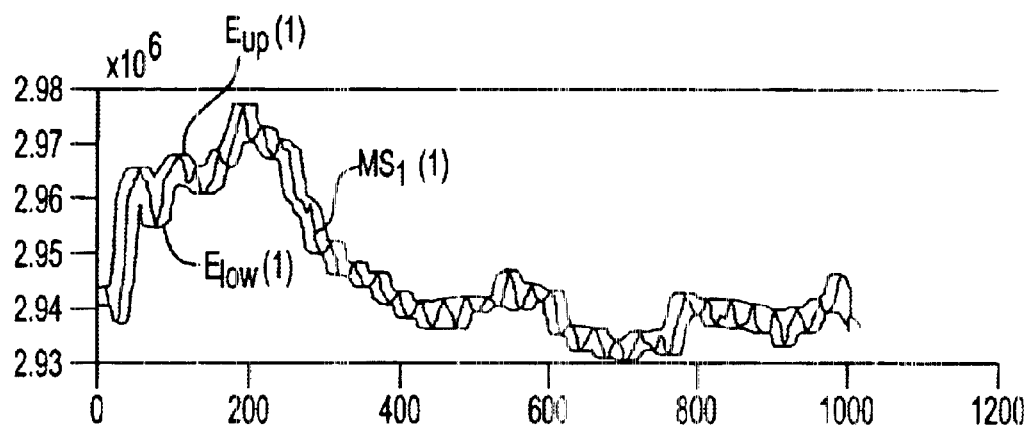
Figure 2B:
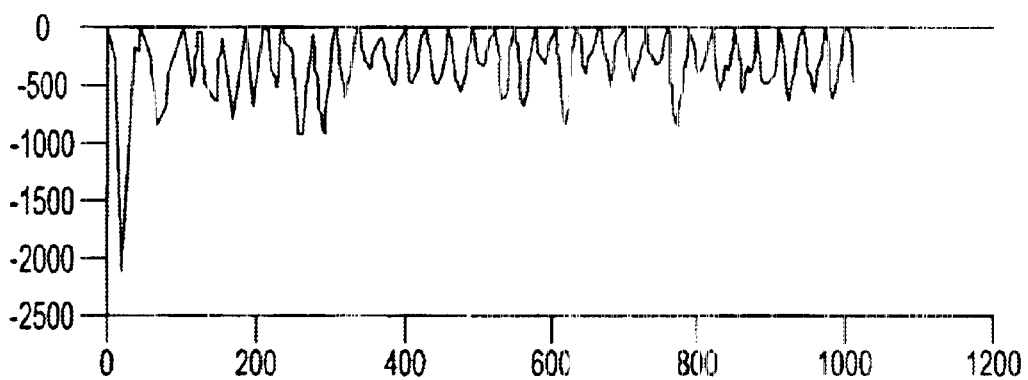
Figure 3A:
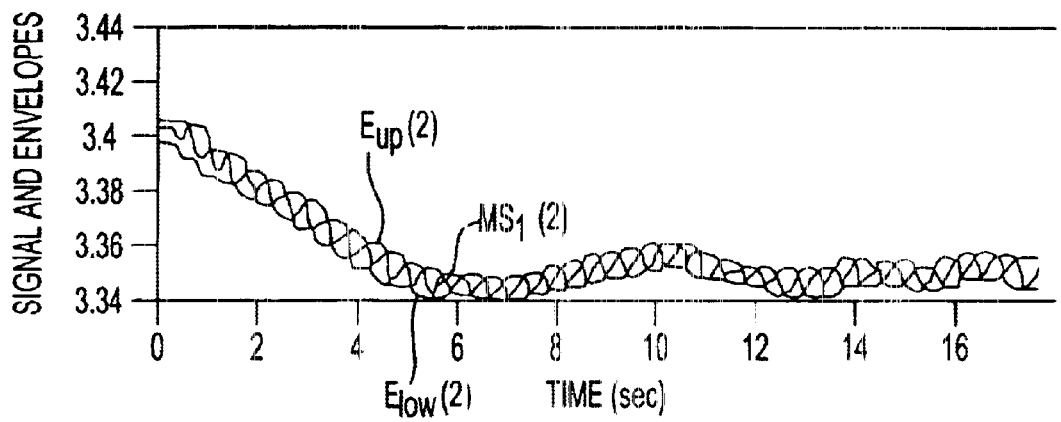
FIGS. 3A–3B and 4A–4B illustrate, respectively, two more examples showing experimental results of the method according to the invention used with the pulse oximetry.
Figure 3B:
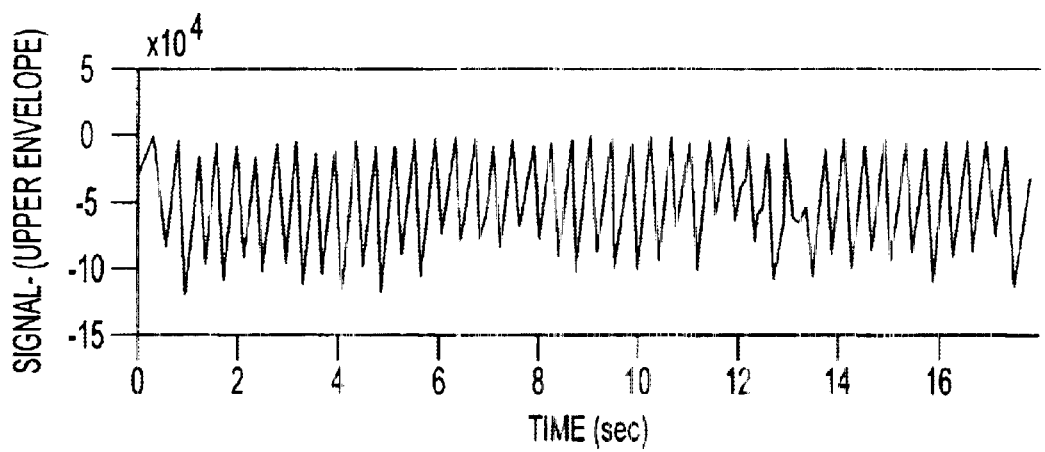
Figure 4A:
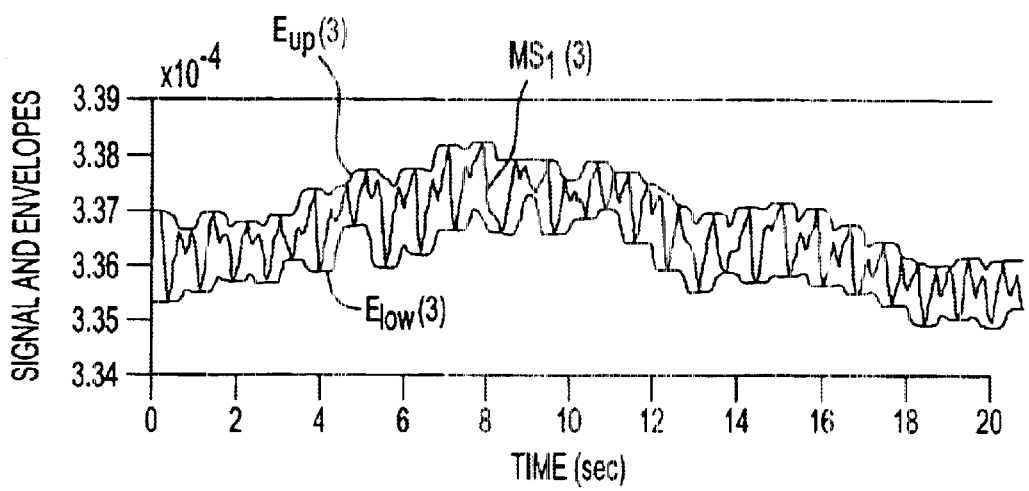

Reference is made to FIGS. 2A–2B, 3A–3B and 4A–4B illustrating three examples, respectively, of processing a measured signal obtained with a pulse oximeter. FIGS. 2A, 3A and 4A illustrate the sampled and frequency filtered measured signals $MS^{(1)}_1$, $MS^{(2)}_1$ and $MS^{(3)}_1$ (each having a signal component representative of a pulsatile blood-related signal distorted by motion and respiration artifacts (noise component)), and upper and lower envelopes $E^{(1)}_{up}$ and $E^{(1)}_{low}$, $E^{(2)}_{up}$ and $E^{(2)}_{low}$ and $E^{(3)}_{up}$ and $E^{(3)}_{low}$ of the measured signals $MS^{(1)}_1$, $MS^{(2)}_1$ and $MS^{(3)}_1$, respectively. As shown in the example of FIG. 2A, the amplitude of the artifacts is about 6 times larger than the pulse amplitude (AC).

In order to calculate the upper and lower envelopes of a signal, the location of the local maximum and minimum values of the periodic signal are first calculated. Then, the values between the local minimum points are estimated producing a continuous line that defines the lower envelope, and the values between the local maximum points are estimated producing a continuous line that defines the upper envelope. The line estimation between extreme points can for example utilize linear interpolation or cubic spline interpolation methods.

Figure 4B:
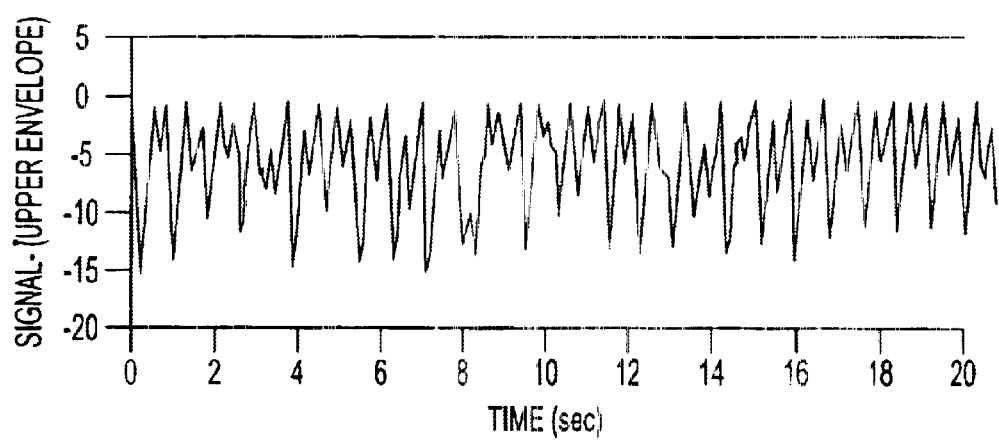
Figure 5A:
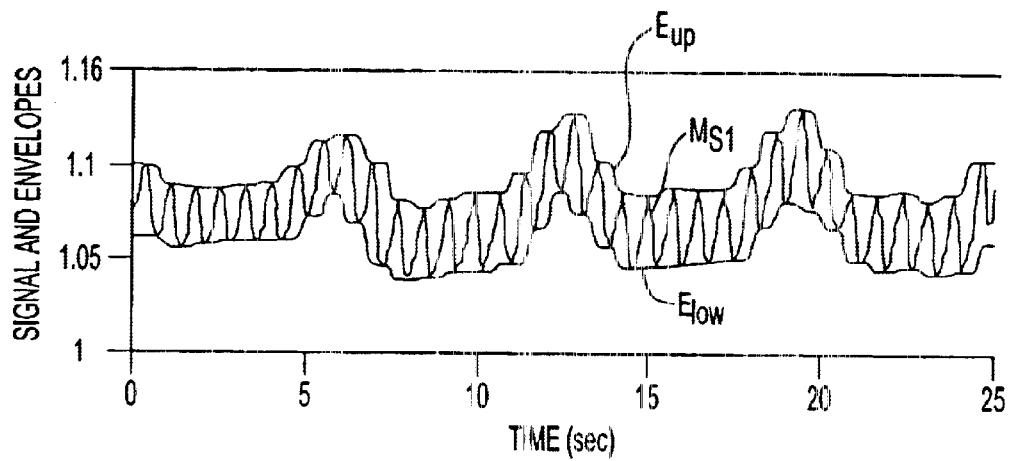
Figure 5B:
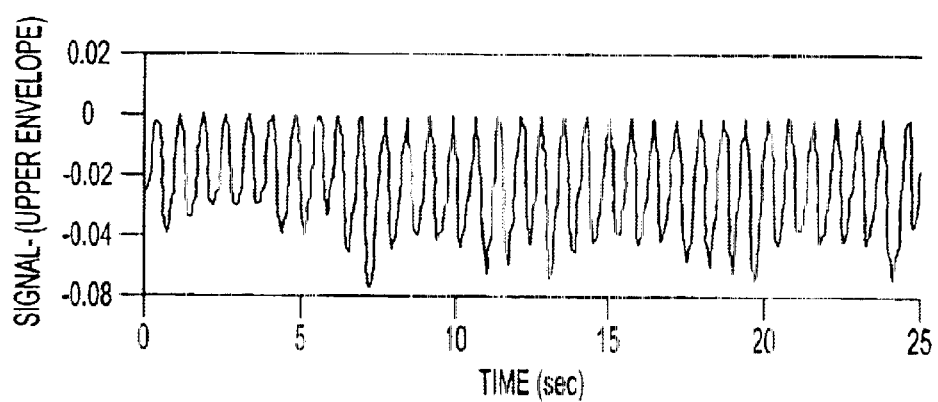
Figure 6A:
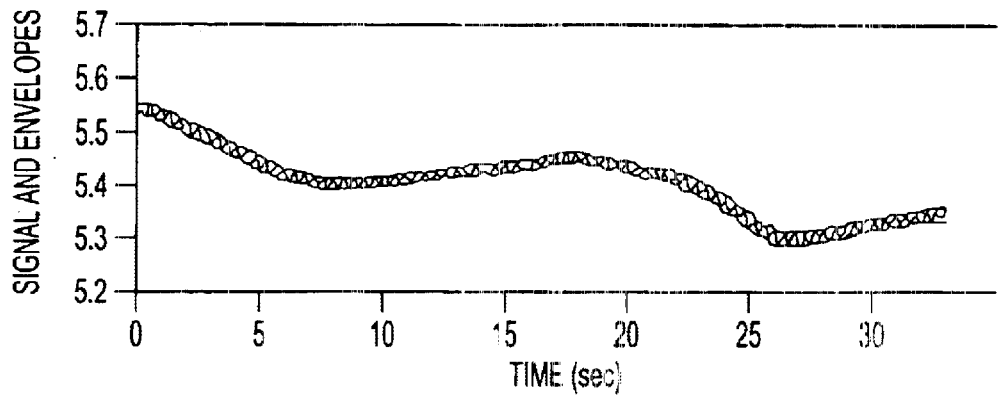
FIGS. 6A–6B, 7A–7B, 8A–8B and 9A–9B illustrate, respectively, four more examples showing experimental results of the method according to the invention used with the bio-impedance technique.
Figure 6B:
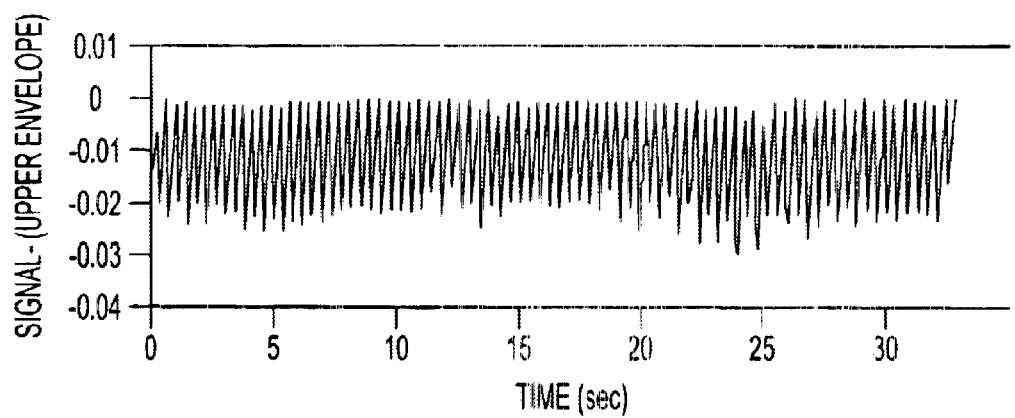
Figure 7A:
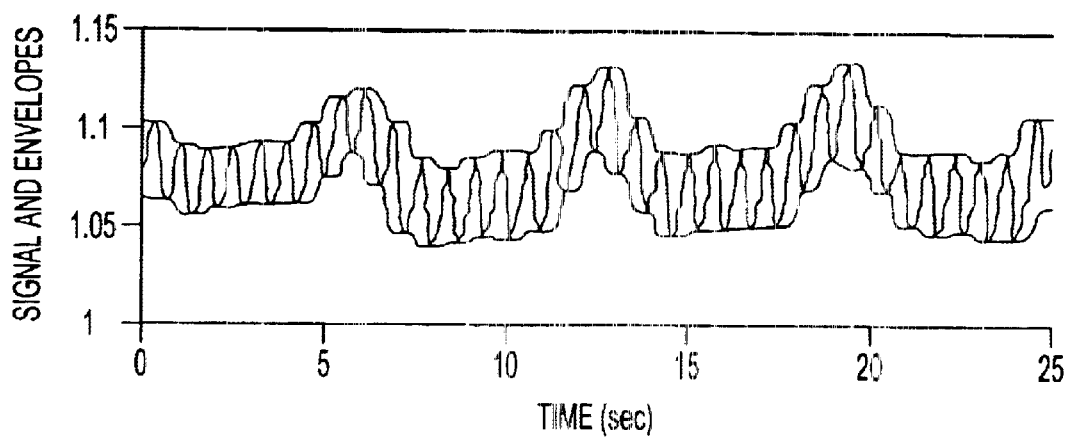
Figure 7B:
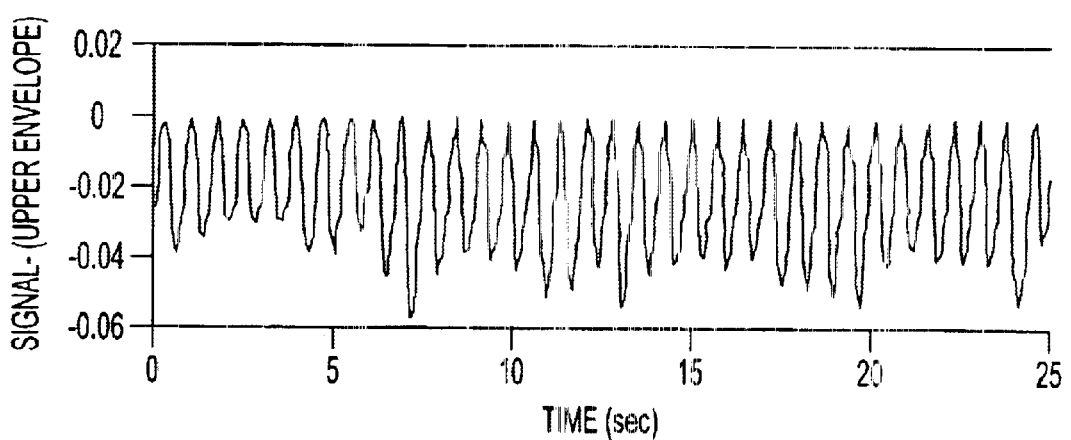
Figure 8A:
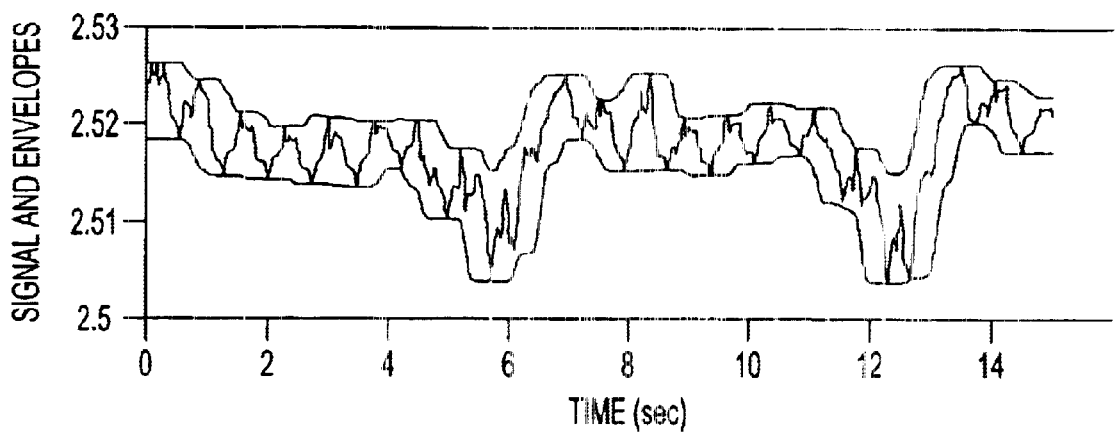
Figure 8B:
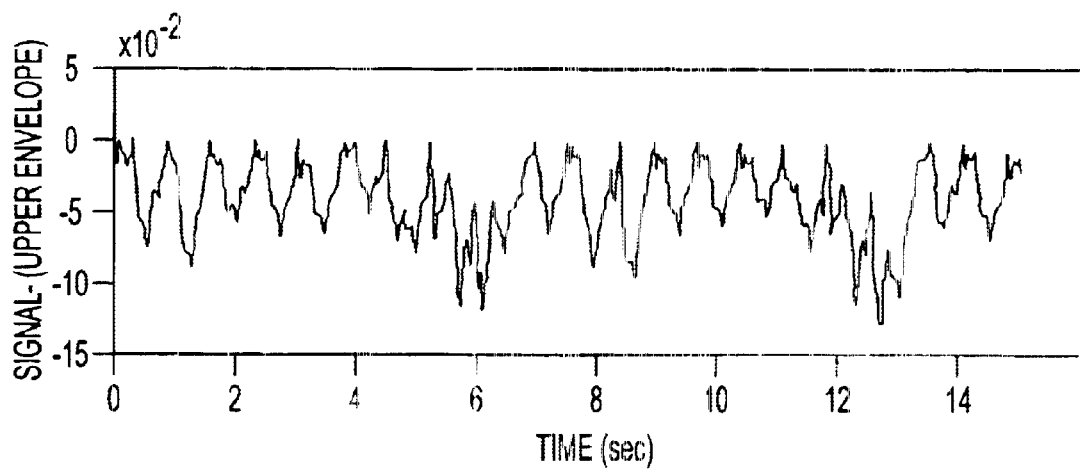
Figure 9A:
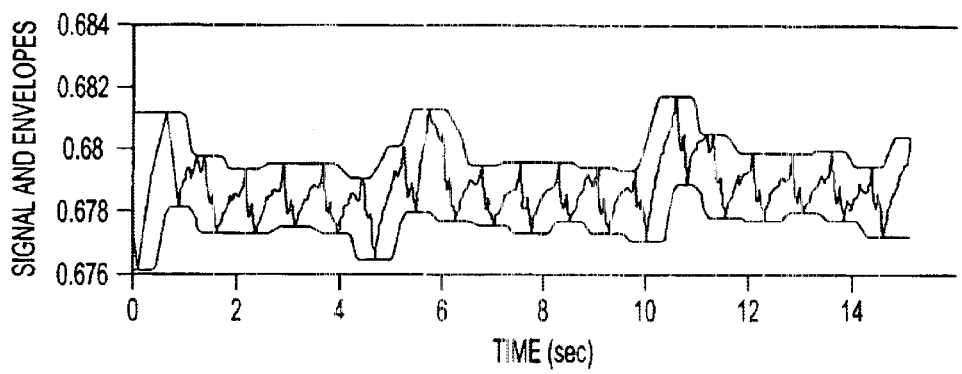
Figure 9B:
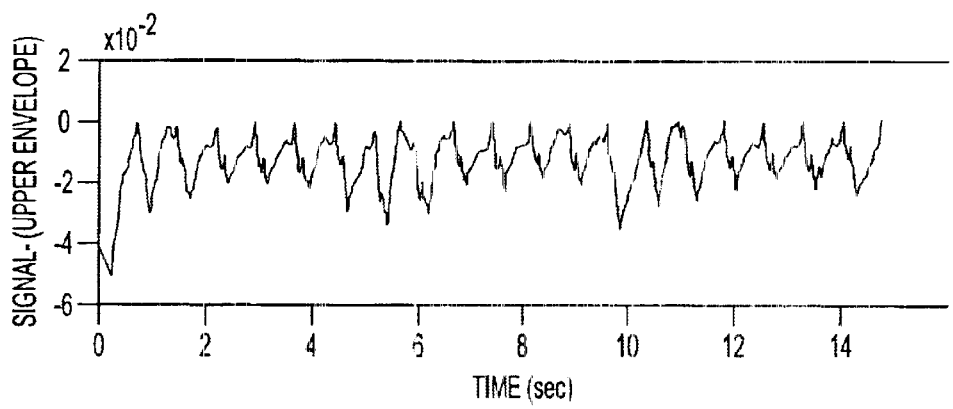

FIGS. 2B, 3B and 4B illustrate (in the enlarged scale) a signal resulting from the subtraction of the upper envelope from the respective measured signal (determination of the difference between the intensity values of the measured signal and the upper envelope for each point in time). As seen, distortions are now smaller than the signal amplitude, and hence, the signal-to-noise ratio is improved (by a factor of 10 in the example of FIGS. 2A–2B).

In order to calculate the amplitude of the blood pulsation (AC component of the pulsatile blood-related signal), the lower envelope value is subtracted from the upper envelope value ($E_{up}$–$E_{low}$) for each time moment, thereby obtaining a vector of the same length as the vector representing the measured signal. Then, the vector values are sorted, and the median is calculated. Thus, according to the present invention, the alternating value (AC component) of a periodic signal with well-defined peak-to-peak intensity value is calculated as:

$$AC=\text{MEDIAN}(E_{up}-E_{low})$$

It should be noted that, according to conventional techniques, extreme points are used to calculate the pulse amplitude. Hence, for a frame of 256 points (about 3 sec), 3 heartbeats are observed (assuming a heart rate of 60 beats per minute), namely, only 3 maximal and 3 minimal values (one for each pulse). The calculation of the amplitudes of 3 pulses in the 3 sec frame enables to obtain only 3 numbers, and the mean amplitude in the frame is calculated from these 3 pulse amplitudes. If the detected signal includes data representative of an additional pulse that does not really exist, this will affect the data analysis results (one wrong amplitude number from three values: two correct values and one false).

On the contrary, the present invention utilizes the statistical analysis of 256 values obtained after the subtraction of the two envelopes to estimate the most likely to appear amplitude in the frame. In order to reduce the influence of artifacts and to find the median of the signal (i.e., amplitude value that is most likely to appear) resulted from the subtraction ($E_{up}$–$E_{low}$), the values are sorted, 10% of the extreme values (the smallest and the largest ones) are excluded, and the median is taken from the remaining values.

FIGS. 5A–5B, 6A–6B, 7A–7B, 8A–8B and 9A–9B illustrate five different examples, respectively, of processing a measured signal obtained with bio-impedance measurements of heart activity in a cardiac output measurement device. Here, FIGS. 5A, 6A, 7A, 8A and 9A show the sampled and frequency filtered measured signals (each having a signal component representative of a pulsatile blood-related signal distorted by motion and respiration artifacts), and upper and lower envelopes of the measured signals. FIGS. 5B, 6B, 7B, 8B and 9B signals with the improved signal-to-noise ratio obtained by subtracting the upper envelopes from the respective measured signals.

Figure 10:
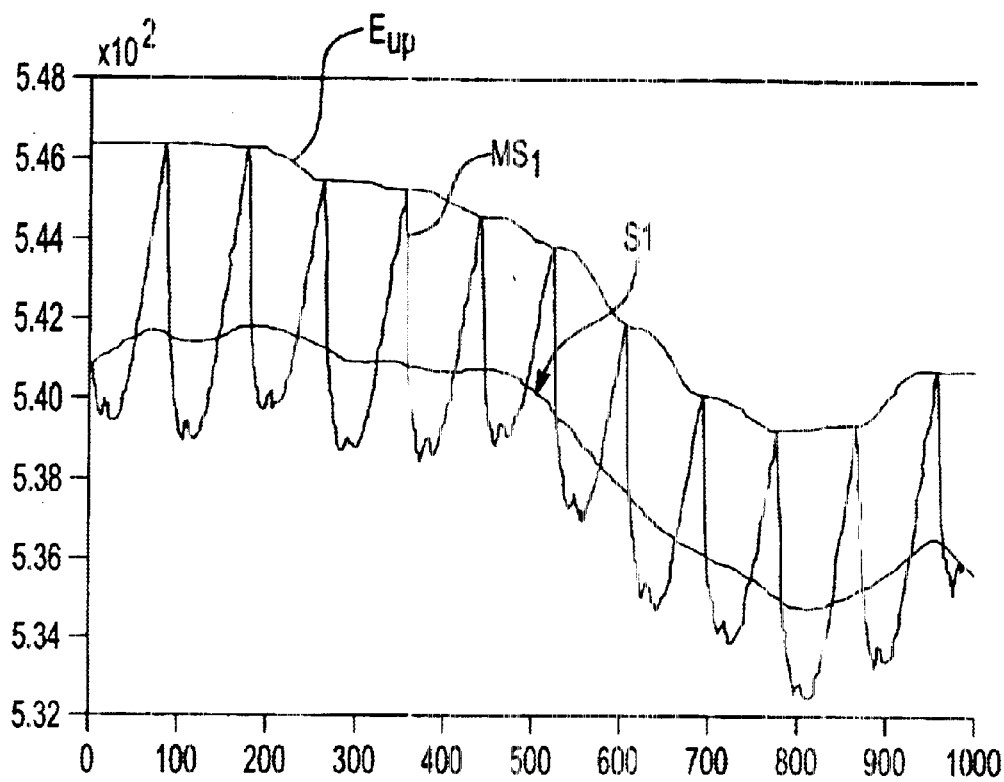
FIG. 10 illustrates the determination of a DC component of the pulsatile signal according to the invented method, as compared to that of the conventional technique.

Calculation of the DC component of a blood-related signal contained in the measured signal $MS_1$ will now be described with reference to FIG. 10. When illuminating the measurement location during the pulse (when blood fills a blood vessel), more of the incident light is absorbed. Therefore, the detected signal reflected from the skin is decreased accordingly (proportional to the light absorption).

According to the conventional approach, the constant value of the reflected light intensity (i.e., the DC component of the photoplethysmogram) is calculated as the average value of a signal $S_1$ measured in the middle of the measured signal $MS_1$. This approach is based on the fact that the average value contains the constant level of reflected light (between arterial pulses) and the pulsation value (AC component). This averaging value is a result of the base line, the amplitude of the pulse, and the shape of the pulse.

According to the technique of the present invention, the real constant absorption component defined by the upper envelope $E_{up}$ of the measured signal $MS_1$ is used to calculate the DC component value, which gives better accuracy, as compared to the conventional approach. Thus, according to the invention, the upper envelope values are sorted, and the median is taken as the DC component, i.e., DC=MEDIAN ($E_{up}$). Alternatively, the DC component of such a periodic signal with well-defined peak-to-peak value may be calculated as the median of the half of the sum of the upper and lower envelope values, i.e., DC=MEDIAN(($E_{up}$+$E_{low}$)/2).

The signal processing according to the invention suitable to be used for the calculation of the heart rate will now be described. This technique is based on the knowledge about the physiological properties of the biophysical signals related to the heart cycle, and consists of a spectral filtering kernel preprocessing in order to enhance the pulse signal from the additive noise and disturbances, thus improving the signal-to-noise ratio. This makes further processing techniques, such as Fast Fourier Transform and auto correlation, more efficient when processing the signal to calculate the heart rate.

Figure 11:
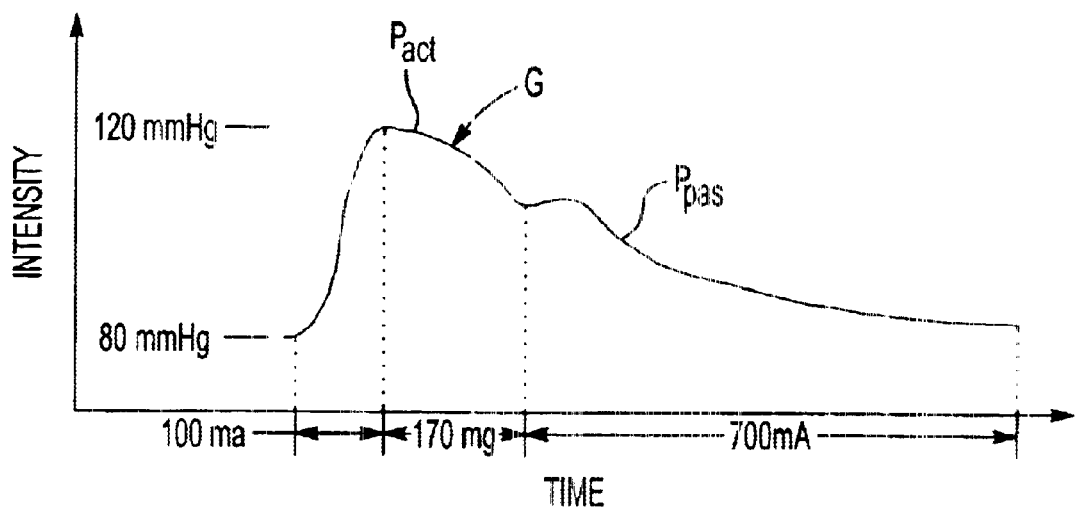
FIG. 11 illustrates the typical shape and timing of a blood pressure pulse in an artery.

FIG. 11 illustrates a graph G of the typical shape and timing of the blood pressure pulse in an artery which represents a biophysical signal related to the change in the blood pressure, induced by the heart cycle, and presents a signal component in the measured signal $MS_2$. This signal component has the active phase (systolic phase) $P_{act}$ and the passive phase (diastolic phase) $P_{pas}$ of the pulse. The duration of the active phase $P_{act}$ is defined by the heart's contraction phase and ranges between 80 and 140 ms, and the duration of the passive phase $P_{pas}$ is the remaining time, i.e., the difference between the heart rate duration and the active phase duration. The typical human heart rate ranges between 40 bpm and 280 bpm, and is equivalent to the frequency range of 0.67–4.7 Hz. In order to filter out noise and artifacts, the pulse oximeter, as well as any other suitable measurement device, typically utilizes filters with the band pass of 0.5–10 HZ. Examining the frequency content of the systolic phase $P_{act}$ in the heart pulse, it is evident that it contains frequencies above 10 Hz. For example, in a 80 ms rising phase, the frequency content of 12.5 HZ is included (i.e., 1/0.08=12.5).

In order to enhance the heart pulse signal, the present invention utilizes the specific asymmetric shape of the blood pressure pulse by adapting the filtering to the fast rising phase of the signal, and thereby distinguishing the pulse signal component from the noise component in the measured signal $MS_2$. In order to prevent disruption of the fast rising phase, the pass band of such an adaptive filter has to include frequencies above 12.5 Hz. As for the lower bound, 0.5 Hz is a proper cut-off frequency, since the heart rate goes down to the frequency of 0.67 Hz, and below this value just a slow artifact takes place, being caused by respiration or motion.

To this end, a special DG Kernel is used based on an analytic function in the form of the Derivative of a Gaussian (DG). The DG Kernel (DGK) analytic equation is:

$$DGK(t) = \frac{-t}{\sigma\sqrt{2\pi\sigma^2}} \exp\left[-\frac{1}{2\sigma^2}t^2\right]$$

wherein t and σ are the time and Gaussian width parameters. These parameters of the DG Kernel function should be matched to the pulse characteristics in order to have the best SNR.

Figure 12:
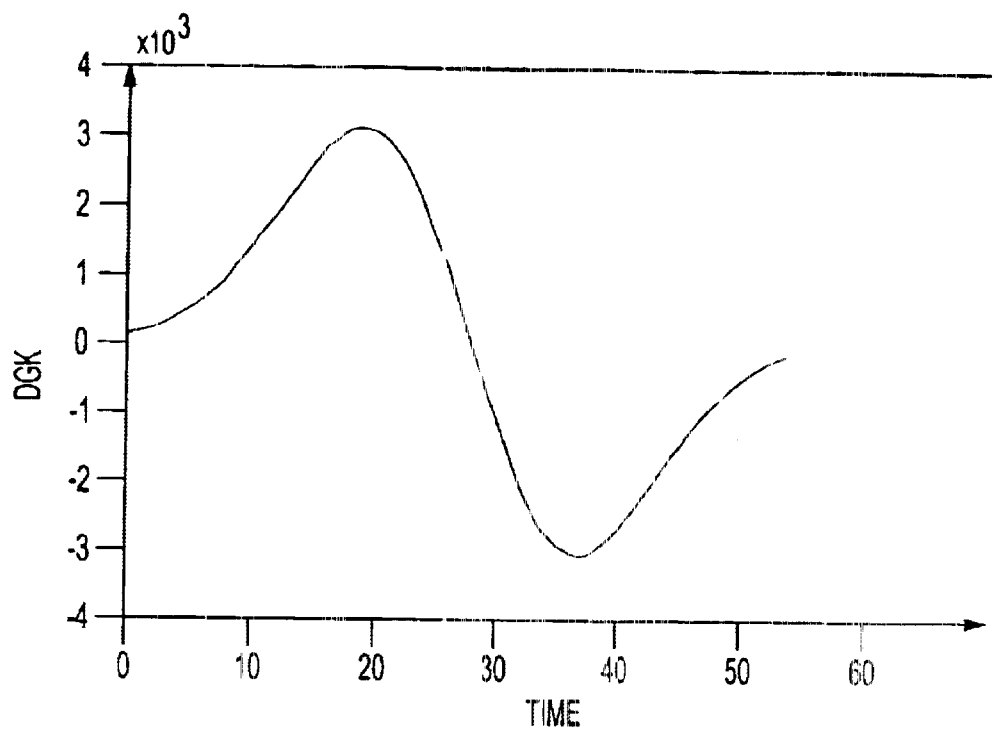
FIG. 12 illustrates the kernel function to be used in a method according to the invention.

FIG. 12 illustrates the function DGK(t). This kind of kernel can advantageously function as a low pass filter to thereby filter high frequency noise. Additionally, this kernel can enhance the signal component in the measured signal when the signal component includes fast slopes at a specific range. This is due to the fact that the derivative operation of the filter is limited to its pass band region. One pass operation of filtering and heart pulse enhancement allow for real time fast determination of the heart rate.

The parameters of this kernel can be adjusted to enhance the systolic phase of the heart pulse signal or even of the QRS segment in an ECG signal, since the frequency content of the QRS segment includes frequencies higher then the frequencies in other segments of the ECG signal. Irrespective of that the shape of the ECG signal is different from the shape of the heart pulse, the DGK can be adapted to enhance the QRS segment relative to other segments in the ECG and to noise and artifacts contained in the ECG measured signal. This technique assists in the detection of the QRS segment, as will be described more specifically further below. Due to the fact that the signal processing according to the invention utilizes the asymmetric property of the pulse signal distinguishing it from other components (noise and artifacts) in the measured signal, the improved signal-to-noise ratio can be obtained, even when the noise and artifact frequency content overlaps with the heart rate frequency.

Thus, the present invention utilizes the Gaussian analytic equation, calculation of the analytic derivative, digitization at the relevant signal sampling frequency, optimization of the length t of the Kernel and the Gaussian width σ for the best performance, and then utilizes the result parameters as a general Finite Impulse Response (FIR) filter parameter. After filtering the measured signal $MS_2$ with the DG Kernel parameters, the energy in the measured signal related to the pulse is enhanced in relation to other artifacts and noise. The general Fast Fourier Transform can then be used to extract the heart rate.

Figure 13A:
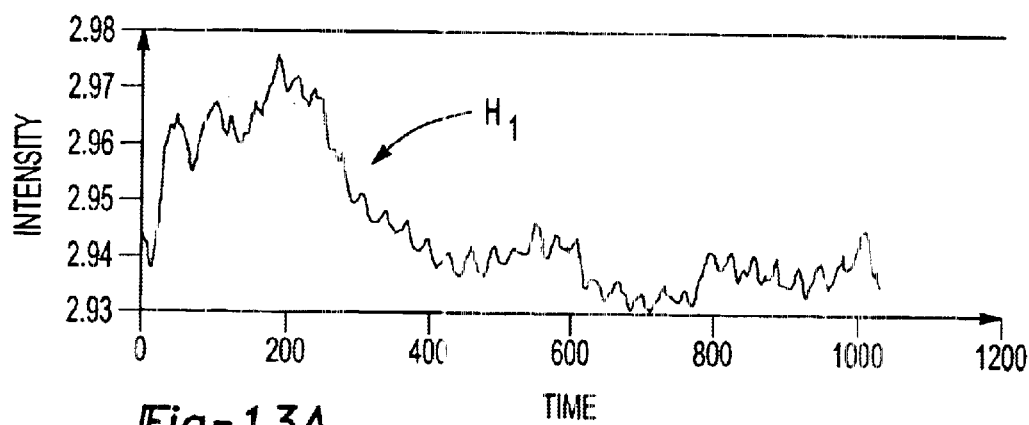
FIGS. 13A and 13B illustrate the experimental results of applying a reflectance pulse oximeter to the patient's chest, presenting a measured signal, respectively, prior to and after the filtering with the kernel function parameters.
Figure 13B:
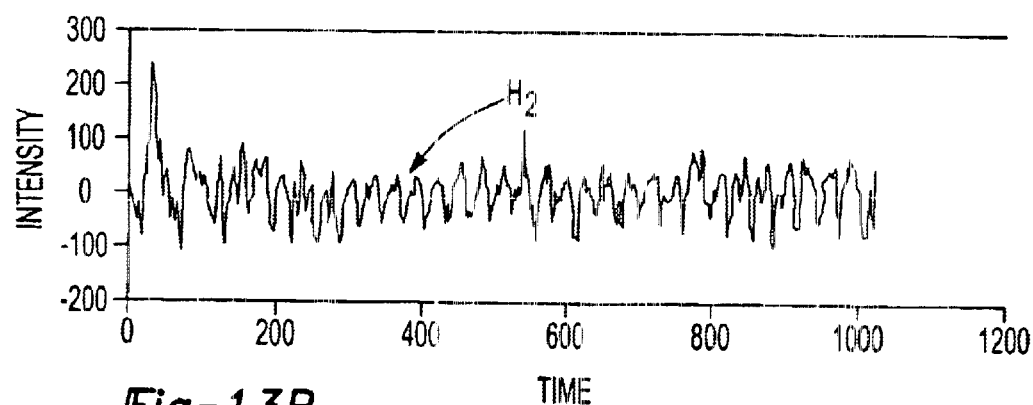

FIGS. 13A and 13B illustrate the experimental results of applying a reflectance pulse oximeter to the patient's chest. FIG. 13A shows a graph $H_1$ presenting the measured signal $MS_2$. Here, respiration and other motion disturbances are presented as relatively slow changes in the signal base line. Heart signals are relatively fast and characterized by periodic small changes in the signal amplitude. It is evident that artifacts are dominant over the heart pulses, as they are about three to four times larger. FIG. 13B illustrates a graph $H_2$ presenting the result of the filtering of the measured signal of FIG. 13A with the DG Kernel parameters. Here, the heart pulses are dominant. Although the pulse amplitudes are modulated by the artifacts' trend, signal-to-noise ratio is significantly improved. As shown, small pulses that were distorted in the signal of FIG. 13A by the artifacts, have proper amplitudes in the signal of FIG. 13B.

Figure 14A:
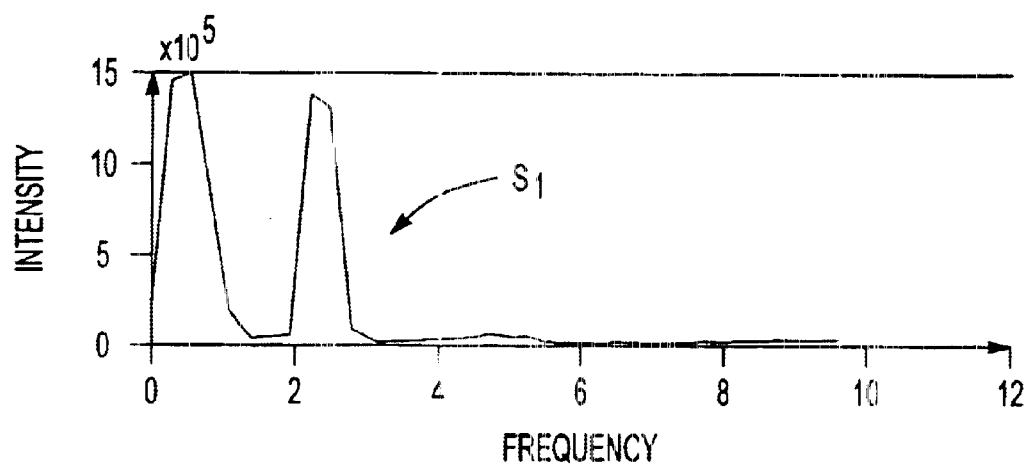
FIGS. 14A and 14B illustrate the spectra of a measured signal, respectively, prior to and after the filtering with DG Kernel parameters.
Figure 14B:
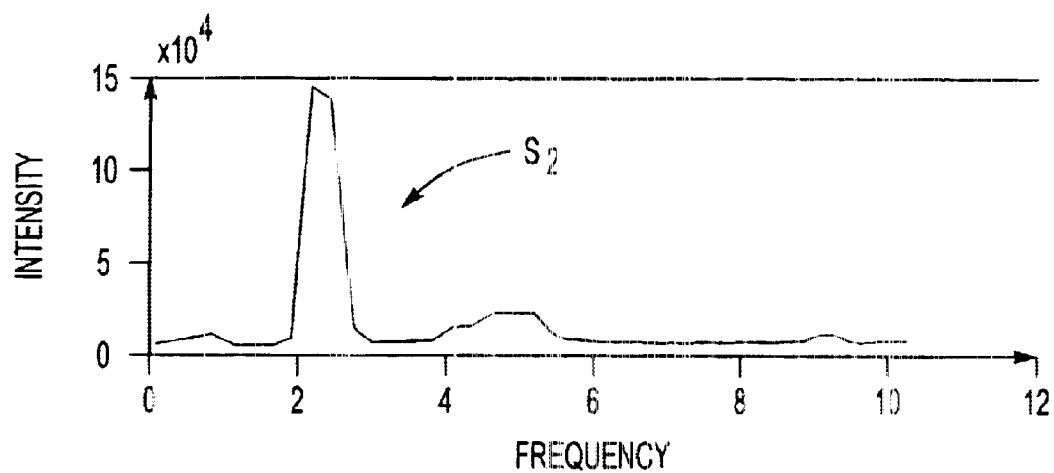

FIGS. 14A and 14B illustrate the spectra $S_1$ and $S_2$ of the measured signal containing an asymmetrically shaped signal component, respectively, prior to and after the filtering with DG Kernel parameters. Comparing these spectra to each other, it is clear that the peak representing the heart rate at 2.2 Hz in much larger than the artifact peaks after the DG Kernel filtering. In other words, the DG Kernel filtering results in the enhancement of the heart rate peak at about 2.2. Hz relative to other double peaks.

Figure 15A:
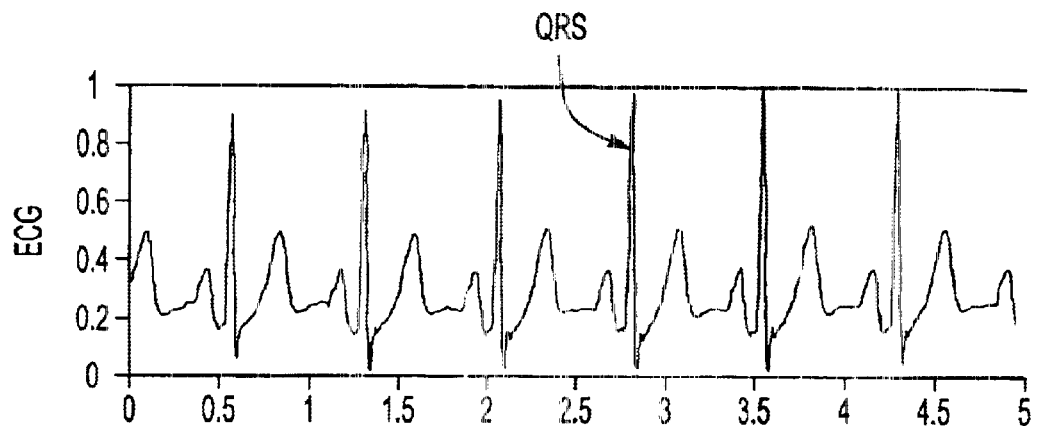
FIGS. 15A and 15B illustrate how the technique of the present invention can be used for enhancement of QRS segment in the ECG signal.
Figure 15B:
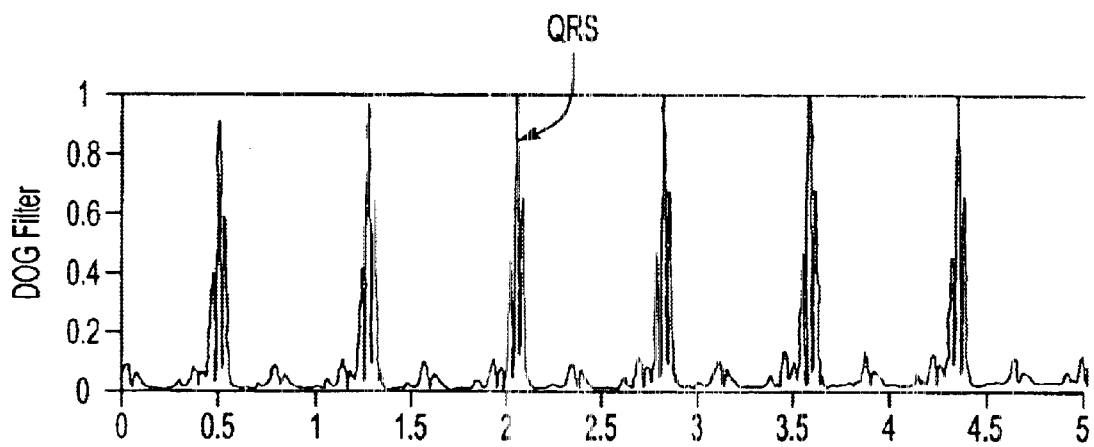

Many medical procedures require detection of the QRS segment of the ECG signal. The use of DG Kernel parameters for filtering enables enhancement of the QRS segment relative to other segments in the ECG signal. FIGS. 15A and 15B illustrate respectively, the typical ECG signal with QRS segment, respectively prior to and after the filtering with the DG Kernel method, showing that the QRS segments are enhanced in the filtered signal.

Turning back to FIGS. 1E and 1F, the DG Kernel method is applied to the measured signal after being frequency-filtered to suppress noise having a frequency other than that of the heart pulse signal. In other words, DG Kernel filtering is applied to the signal in which the noise and artifacts frequency spectra overlap the heart rate frequency spectrum. By this, pulse related information is enhanced, and then a general spectrum method can be applied to obtain the heart rate. The $SpO_2$ level is calculated using the envelope technique: The median of the difference ($E_{up}-E_{low}$) between the upper and lower envelope values is used for the pulse amplitude calculation (AC component of the pulsatile blood-related signal). The median of the upper envelope $E_{up}$ is used for the calculation of the constant detected light (DC component of the pulsatile blood-related signal). The so-obtained AC and DC components are utilized to extract $SpO_2$ according to any suitable conventional technique.

Those skilled in the art will readily appreciate that various modifications and changes can be applied to the embodiments of the invention as hereinbefore exemplified without departing from its scope as defined in and by the appended claims.

What is claimed is:

1. A method for processing a measured signal to extract a signal component and suppress a noise component of the measured signal, wherein the signal component is a substantially periodic signal characterized by a substantially well-defined peak-to-peak intensity value, the method comprising the steps of:
   (i) determining upper and lower envelopes of the measured signal; and
   (ii) analyzing the upper and lower envelope values to extract the signal component from the measured signal, wherein the step analyzing the upper and lower envelope values includes the step of determining a median of the difference between the upper and lower envelope values, as an alternating value in the signal component.

2. The method, as set forth in claim 1, wherein the step of analyzing the upper and lower envelope values includes the step of determining a median of the upper envelope values, as a constant value in the signal component.

3. The method, as set forth in claim 1, wherein the step of analyzing the upper and lower envelope values includes the step of determining a median of the half of the sum of the upper and lower envelope values, as a constant value in the signal component.

4. The method, as set forth in claim 1, wherein the measured signal is a physiological signal.

5. The method, as set forth in claim 3, wherein the signal component is pulsatile blood-related signal.

6. The method, as set forth in claim 5, wherein the pulsatile blood-related signal is indicative of oxyhemoglobin saturation level.

7. The method, as set forth in claim 1, wherein the measured signal is a response of a sample to the application of an external field.

8. The method, as set forth in claim 7, wherein the measured signal is a light response of the sample to incident light.

9. The method, as set forth in claim 7, wherein the sample biological.

10. The method, as set forth in claim 1, for use with a measurement device for non-invasive measurements of patient's blood and heart conditions, the signal component being a pulsatile blood-related signal and containing a signal component characterized by a specific asymmetric shape, the method further comprising the steps of:

defining a kernel function being a derivative of a Gaussian with parameters matching the characteristics of the signal component with the asymmetric shape; and applying spectral filtering to the measured signal with the kernel function, thereby enhancing the signal component characterized by the specific asymmetric shape relative to a noise component in the filtered signal, to thereby enable further processing of the enhanced pulse signal to determine the heart rate.

11. A method for processing a measured signal to extract a signal component and suppress a noise component of the measured signal, wherein the signal component is a substantially periodic signal characterized by a substantially well-defined peak-to-peak intensity value, the measured signal being a physiological signal, the signal component being a pulsatile blood-related signal indicative of oxyhemoglobin saturation level, the method comprising the steps of:

(i) determining upper and lower envelopes of the measured signal; and (ii) analyzing the upper and lower envelope values to extract the signal component from the measured signal, wherein the step of analyzing the upper and lower envelope values includes the step of determining a median of the difference between the upper and lower envelope values as an AC component of the pulsatile blood-related signal, and determining a median of the upper envelope values as a DC component of the pulsatile blood-related signal.

12. A method for processing a measured signal to extract a signal component and suppress a noise component of the measured signal, wherein the signal component is a substantially periodic signal characterized by a substantially well-defined peak-to-peak intensity values the measured signal being a physiological signal the signal component being a pulsatile blood-related signal indicative of oxyhemoglobin saturation level, the method comprising the steps of:

(i) determining upper and lower envelopes of the measured signal; and (ii) analyzing the upper and lower envelope values to extract the signal component from the measured signal, wherein the step of analyzing the upper and lower envelope values includes the step of determining a median of the difference between the upper and lower envelope values as an AC component of the pulsatile blood-related signal, and determining a median of a half of the sum of the upper and lower envelope values as a DC component of the pulsatile blood-related signal.

13. A method for processing a measured signal to extract a signal component and suppress a noise component of the measured signal, wherein the signal component is a substantially periodic signal characterized by a substantially well-defined peak-to-peak intensity value, the method for use with a measurement device for non-invasive measurements of patient's blood and heart conditions, the signal component being a pulsatile blood-related signal and containing a signal component characterized by a specific asymmetric shape and comprising the steps of:

determining upper and lower envelopes of the measured signal;

analyzing the upper and lower envelope values to extract the signal component from the measured signal;

defining a kernel function being a derivative of a Gaussian with parameters matching the characteristics of the signal component with the asymmetric shape; and applying spectral filtering to the measured signal with the kernel function, thereby enhancing the signal component characterized by the specific asymmetric shape relative to a noise component in the filtered signal, to thereby enable further processing of the enhanced pulse signal to determine the heart rate, wherein the step of analyzing the upper and lower envelope values includes the steps of determining a median of the difference between the upper and lower envelope values of the measured signal as an AC component of the pulsatile blood-related signal component, and determining a median of the upper envelope values as a DC component of the pulsatile blood-related signal component.

14. A method for processing a measured signal to extract a signal component and suppress a noise component of the measured signal, wherein the signal component is a substantially periodic signal characterized by a substantially well-defined peak-to-peak intensity value, the method for use with a measurement device for non-invasive measurements of patient's blood and heart conditions, the signal component being a pulsatile blood-related signal and containing a signal component characterized by a specific asymmetric shape and comprising the steps of:

determining upper and lower envelopes of the measured signal;

analyzing the upper and lower envelope values to extract the signal component from the measured signal;

defining a kernel function being a derivative of a Gaussian with parameters matching the characteristics of the signal component with the asymmetric shape; and applying spectral filtering to the measured signal with the kernel function, thereby enhancing the signal component characterized by the specific asymmetric shape relative to a noise component in the filtered signal, to thereby enable further processing of the enhanced pulse signal to determine the heart rate, wherein the step of analyzing the upper and lower envelope values includes the steps of determining a median of the difference between the upper and lower envelope values of the measured signal as an AC component of the pulsatile blood-related signal component, and determining a median of a half of the sum of the upper and lower envelope values as a DC component of the pulsatile blood-related signal component.

15. A pulse oximeter comprising:

(a) a measurement device operable to illuminate a measurement location with incident light of predetermined frequencies, detect a light response of the measurement location to said incident light, and generate a measured signal indicative thereof including a signal component representative of a pulsatile blood-related signal; and (b) a control unit connectable to the measurement device for receiving and processing the measured signal, the control unit comprising a data processing and analyzing utility preprogrammed to determine upper and lower envelopes of the measured signal, and analyze the upper and lower envelope values to extract said pulsatile blood-related signal component from a noise component in the measured signal, wherein the analyzing of the upper and lower envelope values comprises determining a median of the difference between the upper and lower envelope values as an AC component of the pulsatile blood-related signal, and determining a median of the upper envelope values as a DC component of the pulsatile blood-related signal.

16. The pulse oximeter, as set forth in claim 15, for determining a patient's heart rate, the measured signal comprising a blood-related signal component characterized by a specific asymmetric shape, the control unit being preprogrammed to process the measured signal by filtering it with a predefined kernel function being a derivative of a Gaussian with parameters matching the characteristics of said signal component, thereby enhancing said signal component characterized by the specific asymmetric shape relative to a noise component in the filtered measured signal.

17. A pulse oximeter comprising:
(a) a measurement device operable to illuminate a measurement location with incident light of predetermined frequencies, detect a light response of the measurement location to said incident light, and generate a measured signal indicative thereof including a signal component representative of a pulsatile blood-related signal; and
(b) a control unit connectable to the measurement device for receiving and processing the measured signal, the control unit comprising a data processing and analyzing utility preprogrammed to determine upper and lower envelopes of the measured signal, and analyze the upper and lower envelope values to extract said pulsatile blood-related signal component from a noise component in the measured signal, wherein the analyzing of the upper and lower envelope values comprises determining a median of the difference between the upper and lower envelope values as an AC component of the pulsatile blood-related signal, and determining a median of a half of the sum of the upper and lower envelope values as a DC component of the pulsatile blood-related signal component.

18. A method for determining a parameter of a signal, comprising:
(i) determining upper and lower envelopes of the signal, and
(ii) analyzing the upper and lower envelopes to extract a signal component of the signal; and,
(iii) determining the parameter of the signal as a function of the signal component, wherein the step of analyzing the upper and lower envelopes to extract a signal component of the signal includes the step of determining a median of the difference between upper and lower envelope values.

19. A method, as set for in claim 18, wherein the signal component is substantially periodic.

20. A method, as set forth in claim 18, wherein the signal component has a substantially defined peak-to-peak intensity value.

21. A method, as set forth in claim 18, wherein the step of analyzing the upper and lower envelopes includes the step of suppressing noise.

22. A method, as set forth in claim 18, including the steps of applying an external field to a sample and sensing the signal, wherein the signal is a response of the sample to the external field.

23. A method, as set forth in claim 18, including the steps of applying incident radiation to a sample and sensing the signal, where the signal is a response of the sample to the incident radiation.

24. A method, as set forth in claim 23, wherein the parameter of the signal corresponds to a physiological parameter of the sample.

25. A method, as set forth in claim 24, wherein the physiological parameter is pulsatile blood-related.

26. A method, as set forth in claim 24, physiological parameter is oxyhemoglobin saturation.

27. A method, as set forth in claim 18, wherein the median is determined as an alternating value in the signal component.

28. A method, as set forth in claim 18, wherein the median is determined as a constant value in the signal component.

29. A method for determining a parameter of a signal, comprising:
(i) determining upper and lower envelopes of the signal, and
(ii) analyzing the upper and lower envelopes to extract a signal component of the signal; and,
(iii) determining the parameter of the signal as a function of the signal component, wherein the step of analyzing the upper and lower envelopes to extract a signal component of the signal includes the steps of:
determining a median difference between the upper and lower envelope values as an AC component of the signal component; and,
determining a median of the upper envelope as a DC component of the signal component.

* * * * *